(12) United States Patent
Wales et al.

(10) Patent No.: US 10,694,934 B2
(45) Date of Patent: Jun. 30, 2020

(54) DEVICES AND METHODS FOR TISSUE RETRACTION

(71) Applicant: Boston Scientific Scimed, Inc., Maple Grove, MN (US)

(72) Inventors: Ryan V. Wales, Northborough, MA (US); Paul Smith, Smithfield, RI (US); Danny S. Lee, Framingham, MA (US); Scott E. Brechbiel, Acton, MA (US); Jialiang Wang, Smithfield, RI (US); Sean P. Fleury, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 15/938,969

(22) Filed: Mar. 28, 2018

(65) Prior Publication Data
US 2018/0279869 A1    Oct. 4, 2018

Related U.S. Application Data

(60) Provisional application No. 62/478,169, filed on Mar. 29, 2017.

(51) Int. Cl.
*A61B 1/32* (2006.01)
*A61B 17/02* (2006.01)
*A61B 1/00* (2006.01)
*A61B 17/00* (2006.01)
(Continued)

(52) U.S. Cl.
CPC ............ *A61B 1/32* (2013.01); *A61B 17/0206* (2013.01); *A61B 17/0218* (2013.01);
(Continued)

(58) Field of Classification Search
CPC ............ A61B 17/0206; A61B 17/0218; A61B 17/064; A61B 17/0008; A61B 17/083;
(Continued)

(56) References Cited

U.S. PATENT DOCUMENTS 7,524,302 B2 * 4/2009 Tower .............. A61B 17/12136
604/192
8,038,612 B2   10/2011 Paz
(Continued)

FOREIGN PATENT DOCUMENTS

| EP | 2055244 | 5/2009 |
| EP | 2142106 | 1/2010 |
| WO | 9718762 | 5/1997 |

OTHER PUBLICATIONS

International Search Report and Written Opinion dated (Oct. 28, 2018), for PCT/US18/24910 (13 pages).
(Continued)

*Primary Examiner* — Tessa M Matthews

(57) ABSTRACT

The present disclosure relates to the field of tissue dissection. Specifically, the present disclosure relates to medical devices that lift and retract tissue during a dissection procedure to improve visualization of the target tissue and mitigate obstructions for dissection tools. In particular, the present disclosure relates to devices that transition from a constrained to an unconstrained bowed configuration to immobilize and retract the dissected portion of target tissue during a dissection procedure.

20 Claims, 21 Drawing Sheets

(51) Int. Cl.
    *A61B 17/064* (2006.01)
    *A61B 17/08* (2006.01)
    *A61B 17/10* (2006.01)
(52) U.S. Cl.
    CPC .......... *A61B 17/064* (2013.01); *A61B 1/0008* (2013.01); *A61B 17/083* (2013.01); *A61B 17/10* (2013.01); *A61B 2017/0034* (2013.01); *A61B 2017/00269* (2013.01); *A61B 2017/00336* (2013.01); *A61B 2017/00867* (2013.01); *A61B 2017/0225* (2013.01); *A61B 2017/0641* (2013.01); *A61B 2017/0645* (2013.01)
(58) Field of Classification Search
    CPC ............ A61B 1/32; A61B 2017/00269; A61B 2017/00336; A61B 2017/0034; A61B 2017/00867; A61B 2017/0225; A61B 2017/0641; A61B 2017/0645; A61M 1/12; A61M 1/285
    See application file for complete search history.

(56) References Cited

U.S. PATENT DOCUMENTS

| | | | |
|---|---|---|---|
| 8,397,335 B2 | 3/2013 | Gordin et al. | |
| 8,945,155 B2 | 2/2015 | Gordin et al. | |
| 9,463,003 B2 | 10/2016 | Gordin et al. | |
| 10,143,459 B2 | 12/2018 | Heftman | |
| 2010/0057108 A1* | 3/2010 | Spivey | A61B 17/06066 606/144 |
| 2011/0112434 A1* | 5/2011 | Ghabrial | A61B 1/00135 600/564 |
| 2013/0190558 A1* | 7/2013 | Alexander | A61B 1/32 600/37 |
| 2018/0092523 A1* | 4/2018 | Smith | A61B 1/32 |
| 2018/0263614 A1* | 9/2018 | Lee | A61B 17/0206 |
| 2019/0022353 A1* | 1/2019 | Khanicheh | A61M 25/0015 |

OTHER PUBLICATIONS

Sakamoto, N., et al., "Endoscopic submucosal dissection of large colorectal tumors by using a novel spring-action S-O clip for traction (with video)", Gastrointestinal Endoscopy 69(7):1370-1374 (2009).

Fujii, T., et al., "A novel endoscopic suturing technique using a specially designed so-called "8-ring" in combination with resolution clips (with videos)", Gastrointestinal Endoscopy 66(6):1215-1220 (2007).

Matsumoto, K., et al., "T1594: A New Traction Device for Gastric Endoscopic Submucosal Dissecton (ESD): Two-Point Fixed by Latex Traction for Early Gastric Cancer", Gastrointestinal Endoscopy, 71(5):AB317 (2010).

Imaeda, H, et al., "Advanced endoscopic submucosal dissection with traction", World Journal of Gastrointestinal Endoscopy 6(7):286-295 (2014).

Sakamoto, N., et al.," 'Loop Clip' a new closure device for large mucosal defects after EMR and ESD", Endoscopy 40: E97-E98 (2008).

Fujihara, S., et al., "Management of a large mucosal defect after duodenal endoscopic resection", World Journal of Gastroenterology, 22(29):6595-6609 (2016).

Mori, H., et al., "The Loop Clip is Useful for Closing Large Mucosal Defects After Colorectal Endoscopic Submucosal Dissection: a Preliminary Clinical Study", Digestive Endoscopy 23:330-331 (2011).

Tsuji, K., et al., "Recent traction methods for endoscopic submucosal dissection", World Journal of Gastroenterology, 22(26):5917-5926 (2016).

Ritsuno, H., et al., "Prospective clinical trial of traction device-assisted endoscopic submucosal dissection of large superficial colorectal tumors using the S-O clip", Surgical Endoscopy 28:3143-3149 (2014).

Sakamoto, N., et al., "The facilitation of a new traction device (S-O clip) assisting endoscopic submucosal dissection or superficial colorectal neoplasms", Endoscopy, 40:E94-E95 (2008).

Takeda, T., et al., "Traction device to remove an adenoma in the appendiceal orifice by endoscopic submucosal dissection", Endoscopy 45:E239-E240 (2013).

Kato, M., et al., "Technical feasibility of line-assisted complete closure technique for large mucosal defects after colorectal endoscopic submucosal dissection", Endoscopy International Open, 5(1):E11-E16 (2017) DOI: http://dx.doi.org/10.1055/s-0042-121002.

* cited by examiner

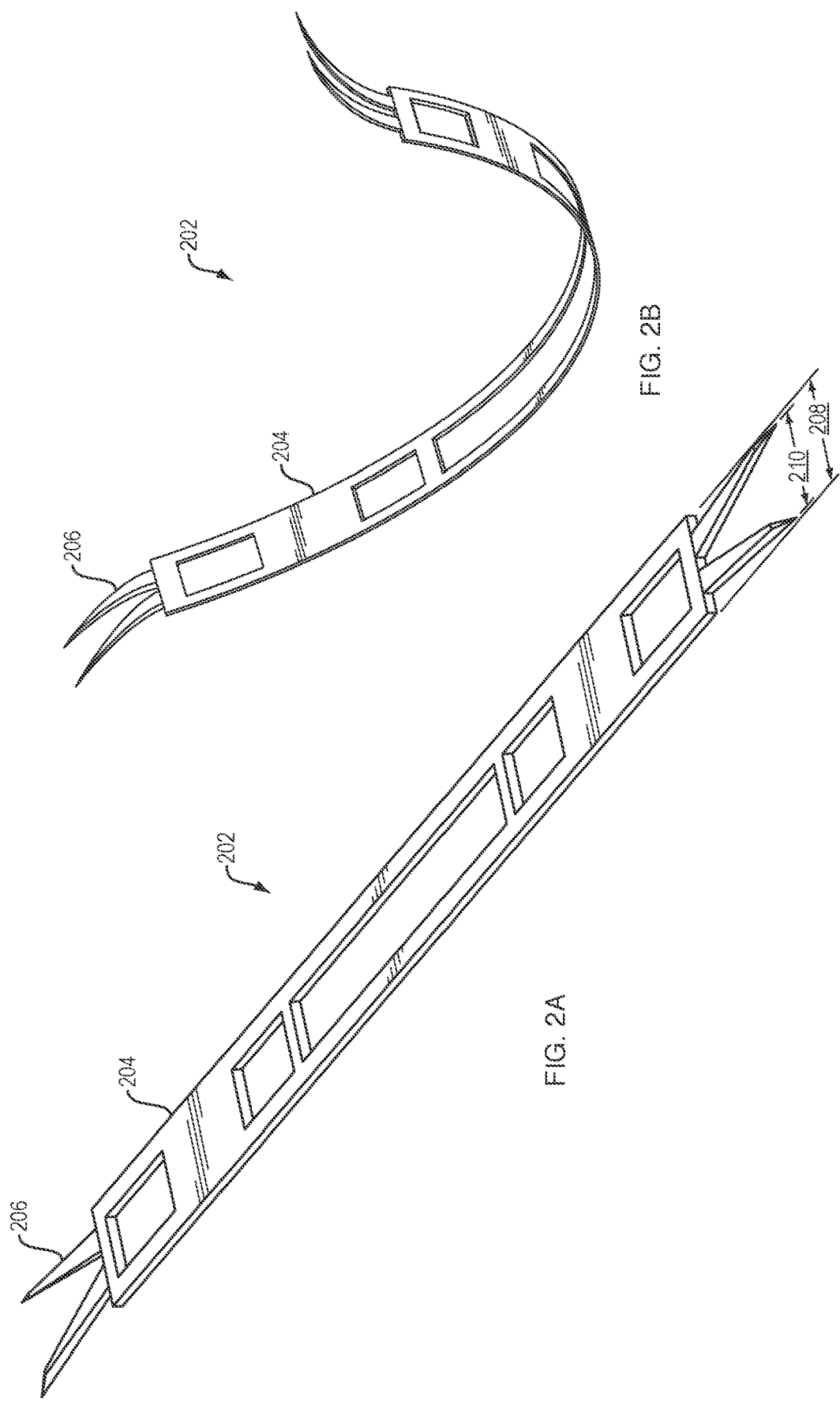

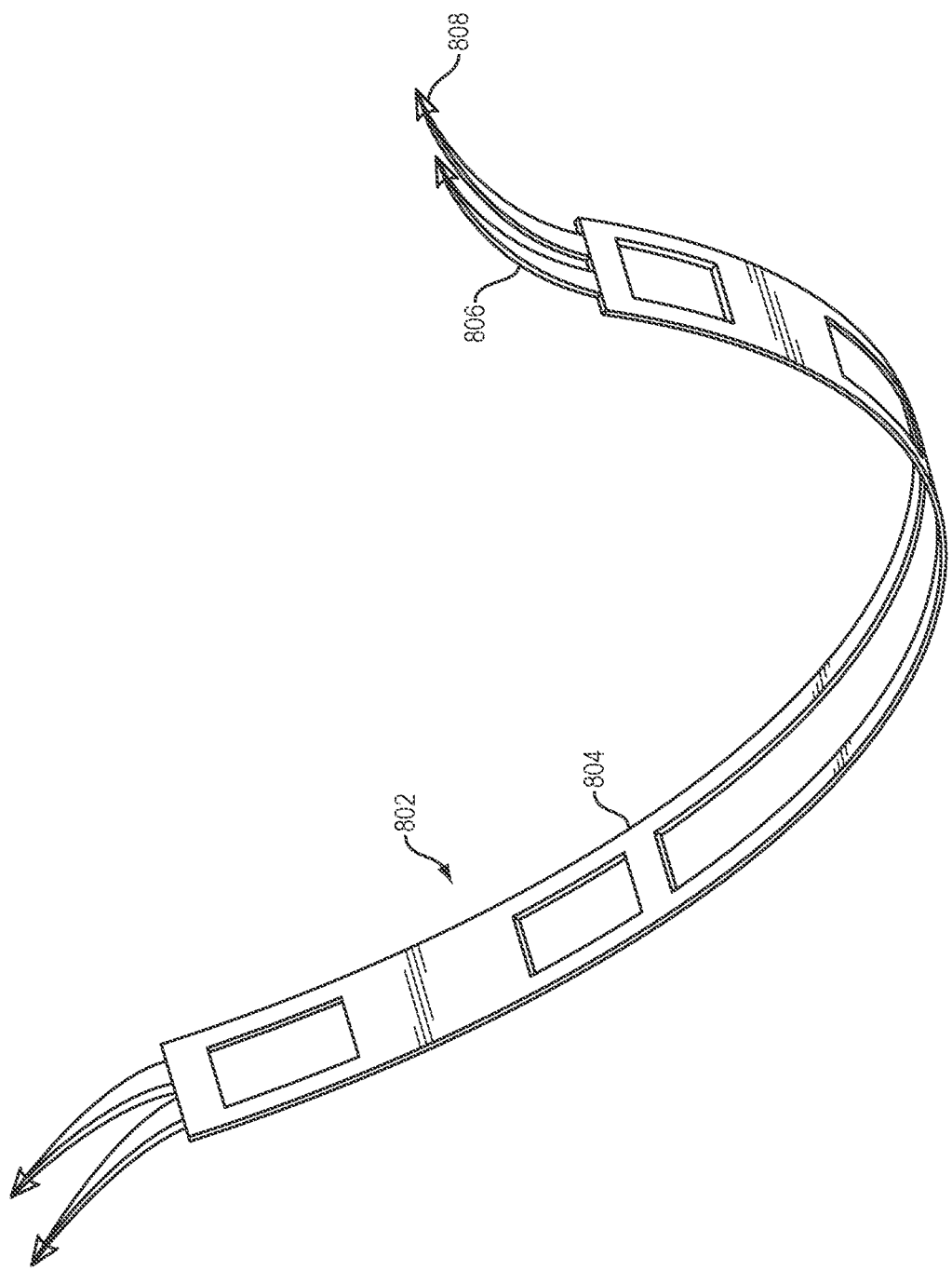

DEVICES AND METHODS FOR TISSUE RETRACTION

PRIORITY

This application claims the benefit of priority under 35 U.S.C. § 119 to U.S. Provisional Patent Application Ser. No. 62/478,169, filed Mar. 29, 2017, which is incorporated by reference herein in its entirety and for all purposes.

FIELD

The present disclosure relates to the field of tissue dissection. Specifically, the present disclosure relates to medical devices that lift and retract tissue during a dissection procedure to improve visualization of the target tissue and mitigate obstructions for dissection tools. In particular, the present disclosure relates to devices that transition from a constrained to an unconstrained bowed configuration to immobilize and retract the dissected portion of target tissue during a dissection procedure.

BACKGROUND

Surgical dissection of lesions from within narrow body passages, such as the digestive tract, may be inefficient and time-consuming due to poor target tissue visualization during the dissection procedure. This problem may be exacerbated during the procedure, as the partially dissected target tissue obstructs the working area to further decrease visibility and obstruct the dissection tools. Therefore, various advantages may be realized by the medical devices and methods for tissue retraction and dissection in the present disclosure.

SUMMARY

The present disclosure, in its various aspects, relates to tissue retraction devices and methods for immobilizing and retracting a target tissue during a dissection procedure for improved tissue visualization and manipulation.

Embodiments of the present disclosure may include a tissue retractor system, with a delivery catheter that may have an inner tubular element with a lumen therethrough, an outer sheath disposed about the inner tubular element, the outer sheath and inner tubular element slidingly disposed relative to each other, and an elongate flexible element configured to transition between a first configuration when constrained and a second bowed configuration when unconstrained. The elongate flexible element may be disposed within the lumen of the inner tubular element, the elongate flexible element and inner tubular element slidingly disposed relative to each other and the outer sheath, and may include a distal end having an end width and may be configured to engage a first target tissue portion. The elongate flexible member may include a proximal end having an end width and may be configured to engage a second target tissue portion. The elongate flexible member may include a body portion having a body width connecting the distal end to the proximal end, wherein the body width may be wider than the end width of the distal end and proximal end, and wherein the lumen of the inner tubular element may have a cross-section that accommodates the body width and the end widths.

A tissue retractor system may include a first portion of a cross-section of a lumen of an inner tubular element that may substantially match a body width of a body portion of a lumen of an inner tubular element. A system with an elongate flexible element may include a second portion of a cross-section of a lumen of an inner tubular element that may substantially match an end width of the distal end and proximal end of the body portion of the elongate flexible element. A system may include an outer sheath that may have a slot, whereby rotating one or both of the outer sheath and the inner tubular element relative to each other to align the slot with a second portion of the cross-section of the inner tubular element allows at least one anchor at an end of the elongate flexible element to deploy radially outward from the outer sheath. A system may include an outer sheath that may have a slot, whereby sliding one or both of the outer sheath and the inner tubular element relative to each other to align the slot with a second portion of the cross-section of the inner tubular element allows at least one anchor at an end of the elongate flexible element to deploy radially outward from the outer sheath. A system may include a sheath with a slot that is wider at a distal end than at a proximal end of the sheath. A system may include an inner tubular element with a second portion cross-section that may be open to a perimeter of the inner tubular element along a longitudinal axis of the inner tubular element. A system may include an outer sheath that may have a slot at a distal end with a width along its length that substantially matches the end widths of an elongate flexible element. A system may include an outer sheath that may have a slot with a width extending along a longitudinal axis of the outer sheath, and wherein the width of the slot substantially matches the end widths of an elongate flexible element. A system may include a cross-section of an inner tubular element that is substantially T-shaped and wherein a first portion of the cross-section is configured to slidingly accept the body portion of an elongate flexible element and a second portion of the cross-section is configured to slidingly accept the distal end and proximal end of an elongate flexible element. A system may include a cross-section of an inner tubular element that is substantially C-shaped and wherein a first portion of the cross-section is configured to slidingly accept the body portion of an elongate flexible element and a second portion of the cross-section is configured to slidingly accept the distal end and proximal end of an elongate flexible element. A system may include a push member slidably disposed within a lumen of an inner tubular element proximal to an elongate flexible element, whereby distal movement of the push member extends and translates the elongate flexible element distally. A system may include a distal end and a proximal end of an elongate flexible element where each may comprise one or more tissue anchors selected from the group consisting of tines, forks, hooks, fingers, barbs, loops and clips.

A tissue retractor system may include a plurality of tissue fasteners. A system may include an elongate flexible element that may have a proximal end and a distal end, each of the ends configured to be engaged by a tissue fastener. A system may include at least one guide member attached to an elongate flexible element, wherein the at least one guide member defines a lumen extending therethrough. A system may include a control wire configured to be slidably received within the lumen of the at least one guide member. An elongate flexible element may transition between a first configuration when the control wire is disposed within the lumen of the at least one guide member, and a second configuration when the control wire is removed from within the lumen of the at least one guide member. A system may include at least one delivery catheter configured to deliver an elongate flexible element and at least one tissue fastener.

A system may include a proximal end of an elongate flexible member with a proximal loop configured to be engaged by one of a plurality of tissue fasteners and a distal end comprising a distal loop configured to be engaged by a different one of the plurality of tissue fasteners. A system may include each of a proximal loop and a distal loop of an elongate flexible element that may be larger than a tissue-grasping portion of each of the plurality of tissue fasteners. A system may include a proximal end of an elongate flexible element that may have a proximal arm configured to be engaged by one of a plurality of tissue fasteners and a distal end that may have a distal arm configured to be engaged by another one of the plurality of tissue fasteners. A system may include an elongate flexible element that may include a pair of substantially parallel elements in a first configuration each with a flexible bow portion that extends substantially away from each other in a longitudinal plane in a second configuration. A system may include at least one arm extending from a body between the proximal and distal ends of an elongate flexible element. A system may include at least one arm that has an end configured to be engaged by a tissue fastener.

An elongate flexible element may include a proximal end and a distal end each with a loop configured to be engaged by a tissue fastener. At least one guide member may be attached to the elongate flexible element, wherein the at least one guide member defines a lumen extending therethrough. A control wire may be configured to be slidably received within the lumen of the at least one guide member. The elongate flexible element may transition between a first configuration when the control wire is disposed within the lumen of the at least one guide member, and a second configuration when the control wire is removed from within the lumen of the at least one guide member. An elongate flexible element may include a pair of substantially parallel elements in a first configuration each with a flexible bow portion that extends substantially away from each other in a longitudinal plane in a second configuration. An elongate flexible element may include at least one arm extending from a body between the proximal and distal ends of the elongate flexible element. An elongate flexible element may include a guide member with a visual marker at an end portion of the guide member.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures:

FIG. 2A is an illustration of an elongate flexible element in a constrained configuration according to an embodiment of the present disclosure.

FIG. 2B is an illustration of the elongate flexible element of FIG. 2A in an unconstrained configuration.

FIG. 8C is an illustration of an elongate flexible element with hooks according to an embodiment of the present disclosure.

Figure 1:
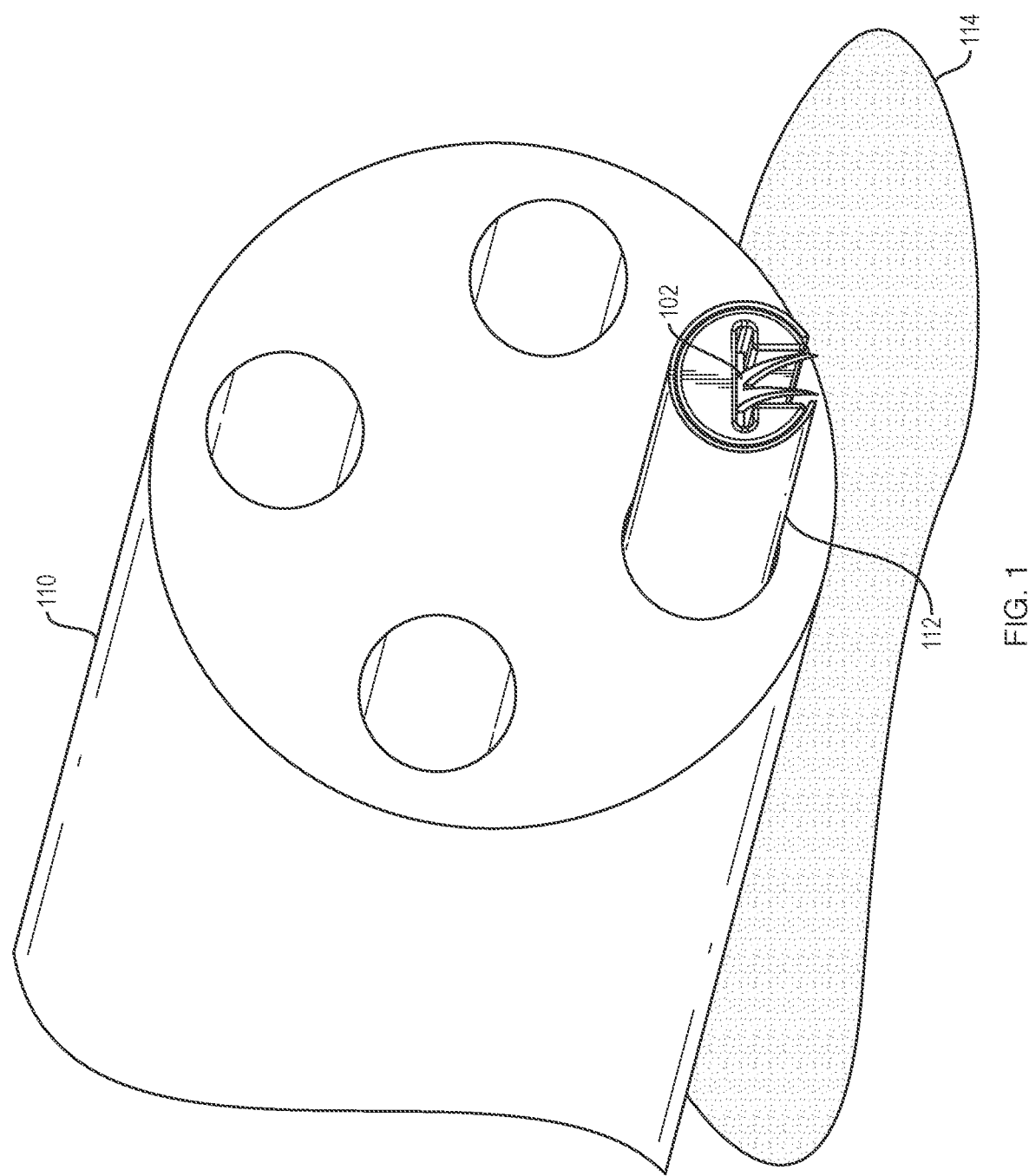
FIG. 1 is an illustration of a system being deployed from an endoscope according to an embodiment of the present disclosure.

It is noted that the drawings are intended to depict only typical or exemplary embodiments of the disclosure. Accordingly, the drawings should not be considered as limiting the scope of the disclosure.

DETAILED DESCRIPTION

The disclosure is not limited to the particular embodiments described, as such may vary. The terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to medical devices and systems and procedures for dissecting tissues of the digestive system, it should be appreciated that such medical devices and methods may be used to dissect tissues of the abdominal cavity, gastrointestinal system, thoracic cavity, urinary and reproductive tract and the like. Moreover, a variety of medical procedures may benefit from the presently disclosed medical devices and procedures, including, for example, Endoscopic Submucosal Dissection (ESD), Peroral Endoscopic Myotomy (POEM), cholecystectomy and Video-Assisted Thoracoscopic Surgery (VATS) procedures. The structures and configurations, and methods of deploying, in order to stabilize, manipulate and provide a clear field of view may find utility beyond dissection.

As used herein, the term "distal" refers to the end farthest away from a medical professional when introducing a device into a patient, while the term "proximal" refers to the end closest to the medical professional when introducing a device into a patient.

As used herein, the term "tissue retraction" or "retraction," refers to the ability to control the position of a tissue during a dissection procedure. For example, "retraction" may allow the dissected portion of a target tissue to be immobilized and lifted away from the dissecting plane to improve visualization of the remaining (i.e., non-dissected) target tissue, while also applying tension to the target tissue for more precise manipulation of the dissecting element.

As used herein, the term "target tissue" refers to an unhealthy, diseased (i.e., cancerous, pre-cancerous etc.) or otherwise undesirable portion of tissue that may be healthy or unhealthy. A "target tissue" may also include tissues that are suspected of being unhealthy or diseased, but which require surgical removal for verification of their disease status by biopsy. It should be appreciated that surgical dissection of a "target tissue" typically includes removal of a portion of the surrounding healthy tissue along the "target tissue" margin to ensure complete removal and minimize the potential for metastasis of left behind or dislodged "target tissue" cells to other body locations.

Embodiments described here may have procedural steps or components in common with, or procedural steps or components may useful here as disclosed in, presently pending and commonly owned U.S. Provisional Patent Application Ser. No. 62/402,649, the disclosure of which is incorporated by reference herein in its entirety.

In one embodiment, the present disclosure provides a tissue retraction device which improves target tissue visibility and access during a dissection procedure by retracting and immobilizing the dissected target tissue portion, including without occupying and/or obstructing a working channel of the endoscope. As illustrated in FIG. 1, in one embodiment, an endoscope 110 may deliver and position a tissue retractor of the present disclosure at a target tissue 114 site. An embodiment may include an elongate flexible element 102 within a delivery catheter 112. The elongate flexible element 102 may be pre-loaded within the delivery catheter 112, or it may be loaded into the deliver catheter 112 while in the endoscope 110 by using a push member to translate the elongate flexible element 102 distally.

An embodiment of an elongate flexible element 202 is illustrated in FIGS. 2A and 2B. The elongate flexible element 202 may include a body portion 204 with a body width 208 that is wider than an end width 210 of an end portion 206. The body portion 204 may be solid or have sections missing to use less material in manufacturing or provide scaffolding to the structure of the body portion 204. FIG. 2A depicts the elongate flexible element in a constrained substantially planar configuration, while FIG. 2B depicts the elongate flexible element in a relaxed, unconstrained, bowed configuration. The relaxed bowed configuration could be created through elastic or plastic deformation of the elongate flexible element 202 in manufacture. Depending on the materials and method of manufacturing for material memory, the substantially planar configuration may not need to be constrained. For example, the elongate flexible element 202 could be heat treated to be stable in either or both configurations, so that it assumes one relaxed configuration at one temperature and transitions to a second relaxed configuration when heated etc. The elongate flexible element may include a variety of lengths depending on the application for which it is being used. For example, in a gastrointestinal application, the length of the elongate flexible element could be approximately 2.8 inches (approximately 7.11 centimeters) when constrained, end to end, and approximately 2.5 inches (approximately 6.35 centimeters) when deployed into target tissue before it transitions to a bowed configuration).

Figure 3A:
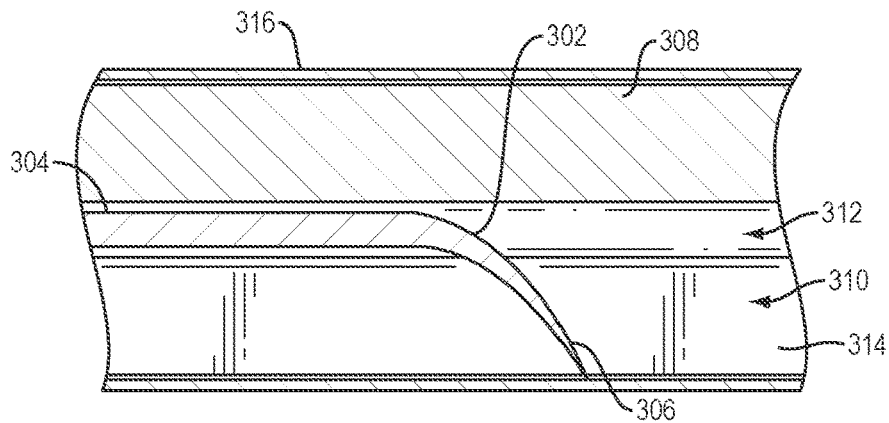
FIG. 3A is an illustration of a side view cross-section of a system according to an embodiment of the present disclosure.
Figure 3B:
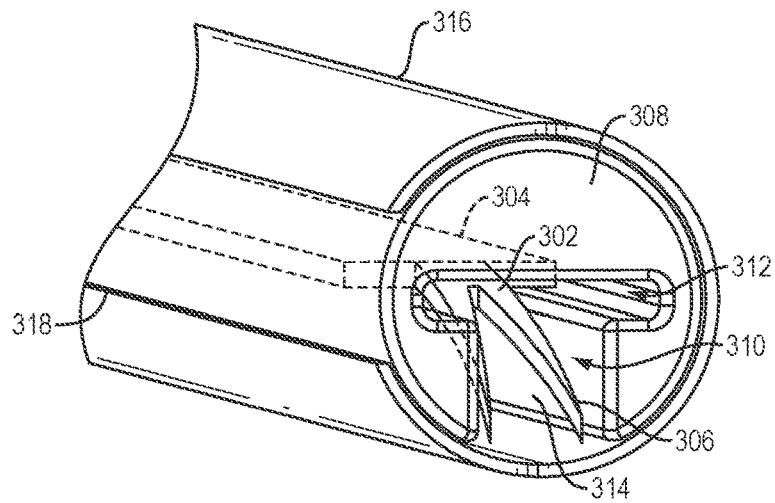
FIG. 3B is an illustration of the system of FIG. 3A in a constrained configuration.
Figure 3C:
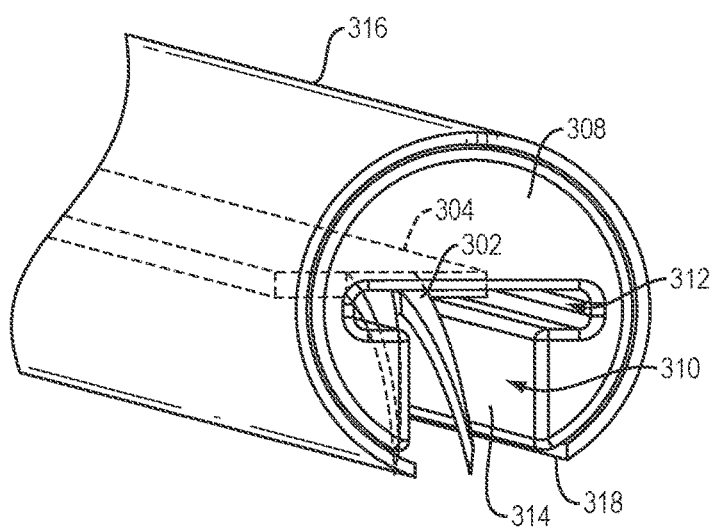
FIG. 3C is an illustration of the system of FIGS. 3A and 3B with an outer sheath in a deployment configuration.

An embodiment of a tissue retraction system of the present disclosure as illustrated in FIGS. 3A-3C may include a delivery catheter comprising an inner tubular element 308 slidably and rotatably disposed within an outer sheath 316. The inner tubular element 308 may include a lumen 310. The lumen 310 slidingly accommodates an elongate flexible element 302. The lumen 410 may run along a portion or the entire length of the inner tubular element 408. The cross-section of the lumen may include a first portion 312 and a second portion 314. The first portion 312 accommodates or may evenly match the width of the body portion 304, while the second portion 314 accommodates or may evenly match the width of the end portion 306. While the elongate flexible element 302 is within the lumen 310 of the inner tubular element, the elongate flexible element 302 may be constrained in a substantially planar configuration. The body portion 304 of the elongate flexible element 302 may lay substantially planar within the first portion 312 of the lumen 310. The end portion 306 may comprise at least one tissue anchor within the second portion 314 of the lumen 310 that is constrained in a radial direction by the outer sheath 316. The elongate flexible element 302 may slidably translate within the lumen 310 while the body portion 304 maintains a substantially planar configuration within the first portion 312 of the lumen and the end portion 306 is constrained radially by the outer sheath 316, as shown in FIG. 3B. The outer sheath 316 in this embodiment includes a slot 318 that runs along the longitudinal axis of the outer sheath 316. The length of the slot may vary up to and including the length of the entire elongate element length. The width of the slot 318 is at least larger than the end portion at some point toward the distal end of the slot, but may be substantially similar (e.g., only slightly larger compared) to the width of the end portion 306 of the elongate flexible element 302. Since the outer sheath 316 constrains the end portions 306 from extending radially outward, the outer sheath 316 may release the end portions 306 when the slot 318 is axially rotated to line up with the second portion 314 of the lumen 310, as shown in FIG. 3C.

A medical professional may position the delivery catheter (i.e., the outer sheath 316 and the inner tubular element 308) containing the elongate flexible element 302 in proximity to the target tissue he or she wishes to retract. This position may place the end portions 306 of the elongate flexible element 302 near the border of the target tissue 320 for which the medical professional has already initiated dissection or plans to dissect. Once the end portions 306 are in close proximity to the desired position, the medical professional may slide and/or rotate the outer sheath 316 with respect to the inner tubular element 308, thereby lining up the slot 318 with the second portion 314 of the lumen 310 and releasing the end portions 306 from inside the outer sheath 316 and into the target tissue 320. The end portions 306 of the elongate flexible element 302 may be released out of the lumen 310 upon rotation and/or sliding of the outer sheath 316 with respect to the inner tubular element 308 and/or the elongate flexible element 302 may be released by translating it distally within the lumen 310 through the use of a push member within the lumen 310, proximal to the elongate flexible element 302. The distal end portion 306 may be released at the same time as the proximal end portion when exposed to the slot 318, or the distal end portion 306 may be released first into the target tissue 320 before the proximal end portion. The push member may translate the distal end portion 306 out of the lumen 310 by being exposed to the slot 318 of the outer sheath 3016 first, and by further translating the push member (and therefore the elongate flexible element 302), the proximal end portion may then be released into the target tissue 320 similar to how the distal end portion 306 was released by being exposed to the slot 318.

Figure 3D:
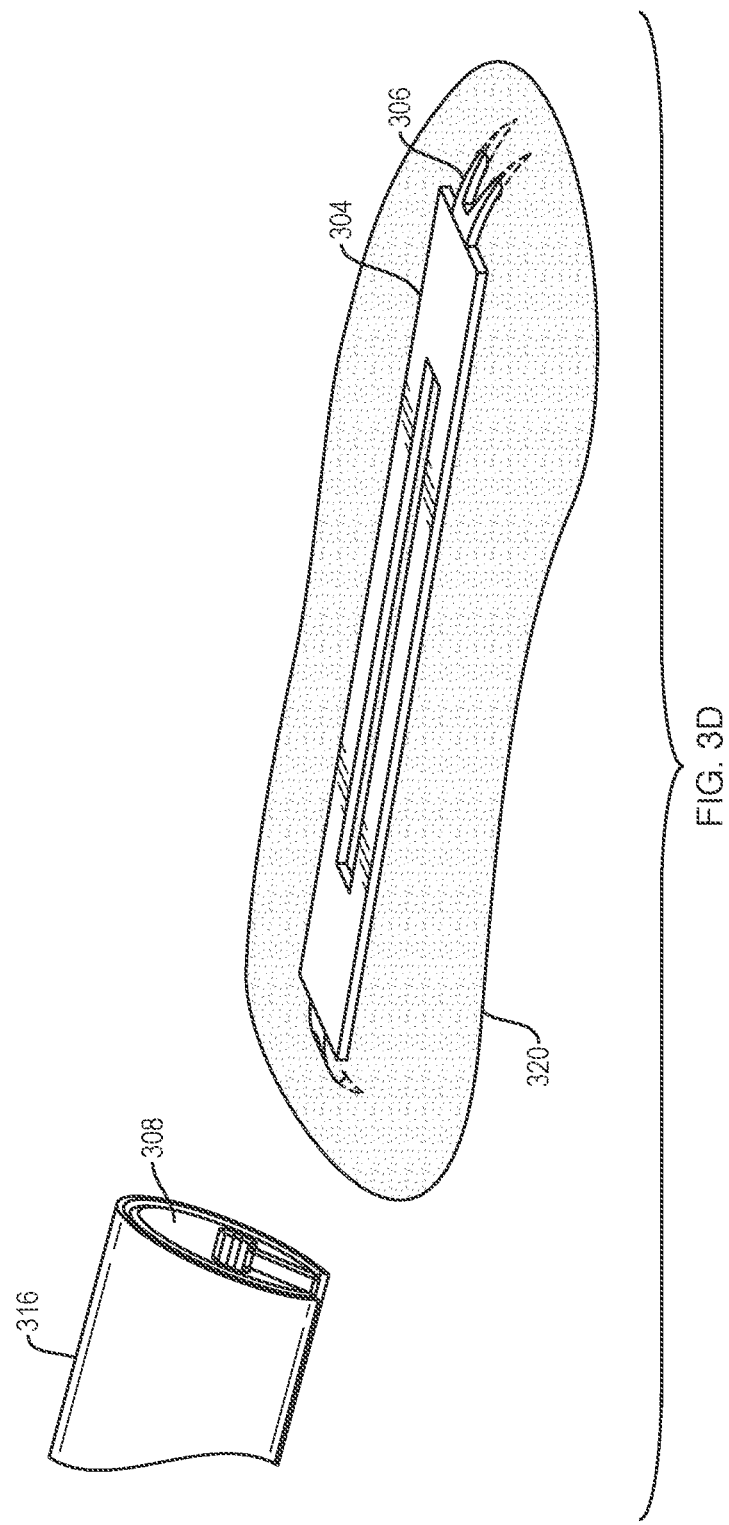
FIG. 3D is an illustration of the system of FIGS. 3A-3C with the elongate flexible element deployed.
Figure 3E:
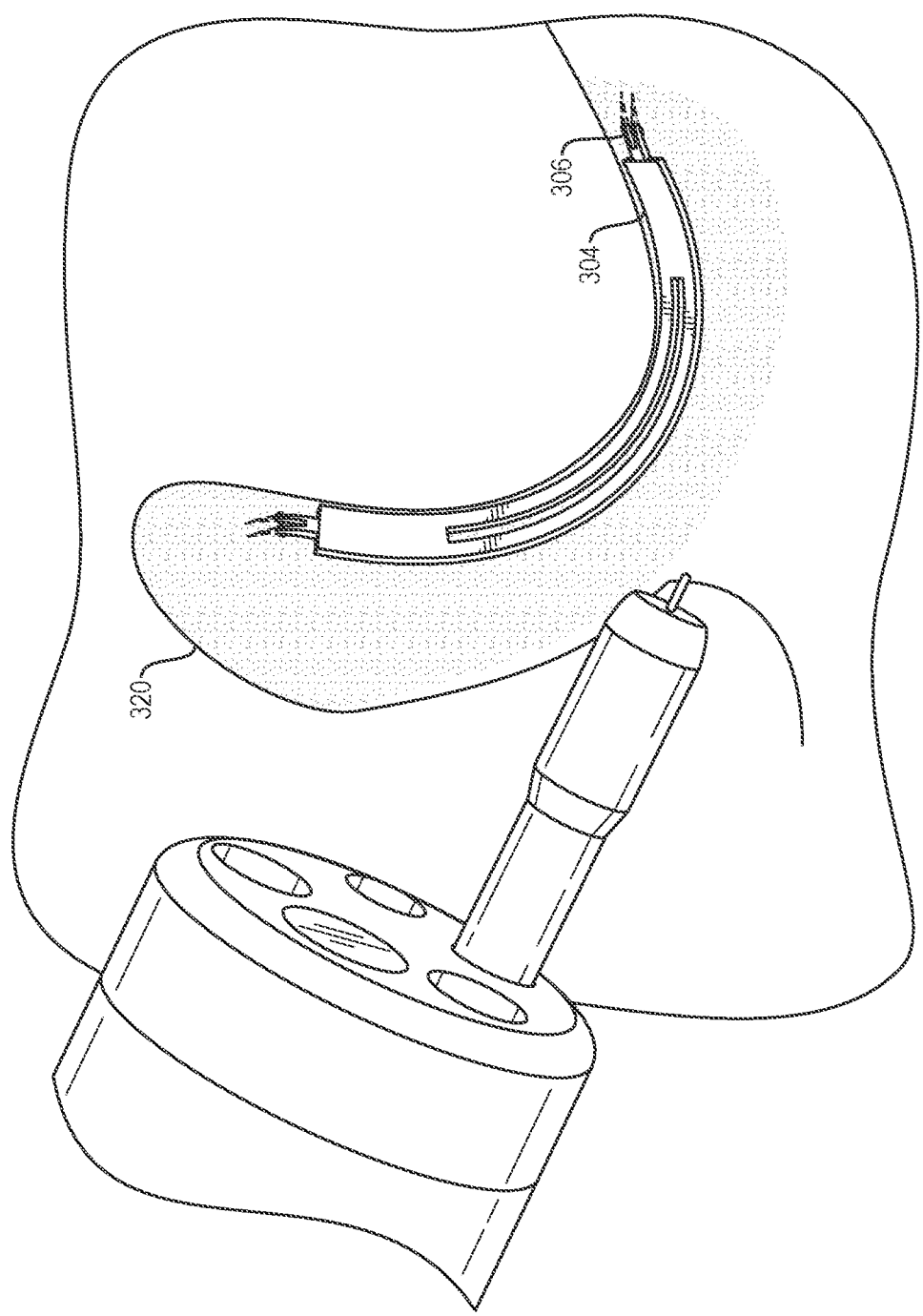
FIG. 3E is an illustration of the system of FIGS. 3A-3D with a dissecting element removing target tissue to be dissected.

Alternatively, the distal end portion 306 may be released into a distal portion of the target tissue 320 by exposing the distal end portion 306 to the slot 318 of the outer sheath 316 and/or using a push member to translate the elongate flexible element 302 distally such as to expose the end portion 306 to engage the distal portion of the target tissue 320. With the distal portion 306 engaged with the target tissue 320 and the proximal end portion still within the lumen 310, the inner tubular element 308 and/or the outer sheath 316 may be retracted until the proximal end portion of the elongate flexible element 302 is exposed to the slot 318 and released into the target tissue 320. This may also be achieved by an alternative outer sheath 316 without a slot 318 by sliding the outer sheath 316 and the inner tubular element 308 with respect to each other until the end portions 306 translate outside of the outer sheath 316 to engage the target tissue. This may also be accomplished through use of a push member to translate the elongate flexible element 302 through the lumen 310. The distal end portion 306 of the elongate flexible element 302 stays embedded into the target tissue 320 while the inner tubular element 308 and/or the outer sheath 316 are retracted such that the rest of the elongate flexible element 302 within the lumen 310 is translated out of the lumen 310, thereby engaging a proximal portion of the target tissue 320 with a proximal end portion of the elongate flexible element 302. With the elongate flexible element 302 delivered into position, the deliver catheter may then be retracted proximally away from the target tissue 320 as illustrated in FIG. 3D. The medical professional may then dissect the target tissue 320, while the elongate flexible element 302 transitions to the bowed configuration as it is unconstrained and the target tissue is dissected away from the remaining tissue as illustrated in FIG. 3E.

Figure 4A:
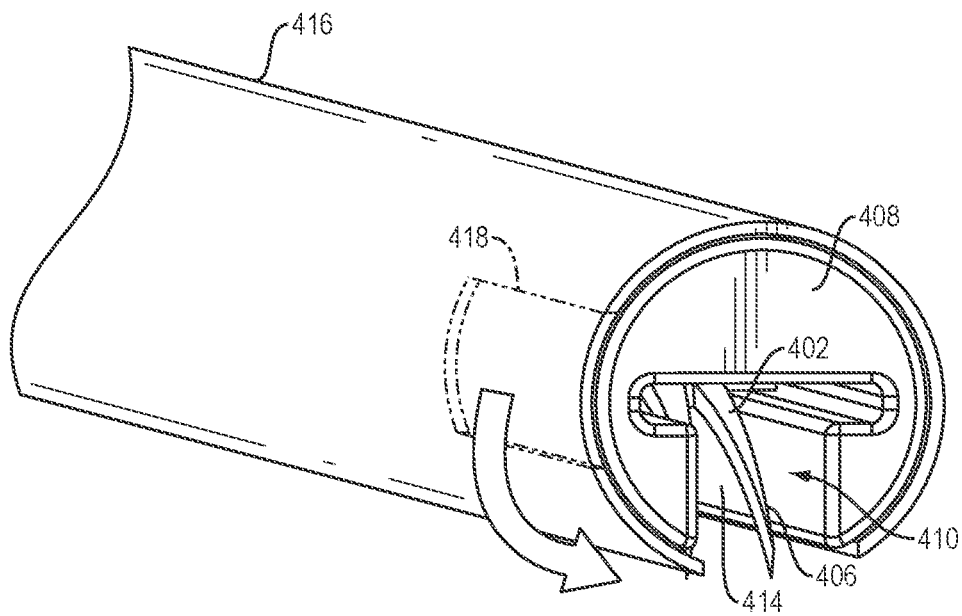
FIG. 4A is an illustration of a system with a slot at a distal end of an outer sheath and an inner tubular element with a lumen cross-section having a first portion and a second portion that together are T-shaped according to an embodiment of the present disclosure.
Figure 4B:
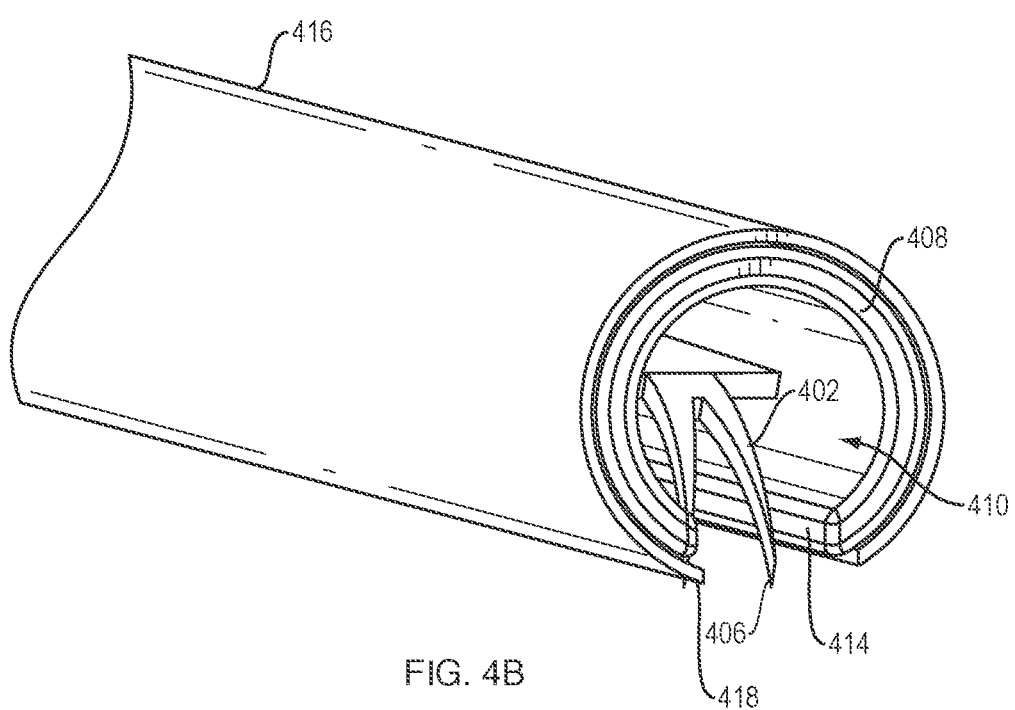
FIG. 4B is an illustration of a system with a slot at a distal end of an outer sheath and an inner tubular element with a lumen cross-section having a first portion that is C-shaped and a second portion that is tangentially open to the perimeter of the inner tubular element according to an embodiment of the present disclosure.

Embodiments of a tissue retraction system of the present disclosure, as illustrated in FIGS. 4A and 4B, may include a slot 418 at a distal end of an outer sheath 416 that extends only a short distance (e.g., less than the length of an elongate flexible element) along the longitudinal axis of the outer sheath 416. When the medical professional has placed a distal end of the delivery catheter (i.e., the outer sheath 416 and the inner tubular element 408) in proximity to a desired position of target tissue for the distal end portion 406 of the elongate flexible element 402, the outer sheath 416 may be rotated and/or slid with respect to the inner tubular element 408 such that the slot 418 matches up with a second portion 414 of the lumen 410, thereby releasing the distal end 406 of the elongate flexible element 402 into the target tissue. This may also be achieved by an alternative outer sheath 416 without a slot 418 by sliding the outer sheath 416 and the inner tubular element 408 with respect to each other until the end portions 406 translate outside of the outer sheath 416 to engage the target tissue. This may also be accomplished through use of a push member to translate the elongate flexible element 402 through the lumen 410. FIG. 4A depicts an inner tubular element 408 with a lumen 410 cross-section having a first portion and a second portion that together are T-shaped. FIG. 4B depicts an inner tubular element 408 with a lumen 410 cross-section having a first portion that is C-shaped and a second portion that is tangentially open to the perimeter of the inner tubular element. The lumen 410 may run along a portion or the entire length of the inner tubular element 408. With the slot 418 at a distal end of the outer sheath 416, a proximal end of elongate flexible element 402 is still constrained against the outer sheath 416 within the lumen 410. With the distal end portion 406 embedded within a first portion of the target tissue and the proximal end of the elongate flexible element 402 still within the lumen 410, the medical professional may place the proximal end portion of the elongate flexible element 402 in proximity to a desired position of a second portion of the target tissue, while the end portion is still within the inner tubular element 408. The medical professional may then translate the outer sheath 416 proximally with respect to the inner tubular element 408 (and/or translate the inner tubular element 408 distally with respect to the outer sheath 416) such that the proximal end of the elongate flexible element 402 matches up with the slot 418, thereby releasing the proximal end into the second portion of the target tissue. Alternatively or additionally, the element 402 may be pushed distally with a push member while optionally pulling back the outer sheath 416 or the inner tubular element 408 and outer sheath 416, or inner tubular element 408 and outer sheath 416 may be retracted, while holding the elongate flexible element 402 from moving proximally with a push member, in each case until the proximal end reaches the slot 418 and is released.

Figure 5:
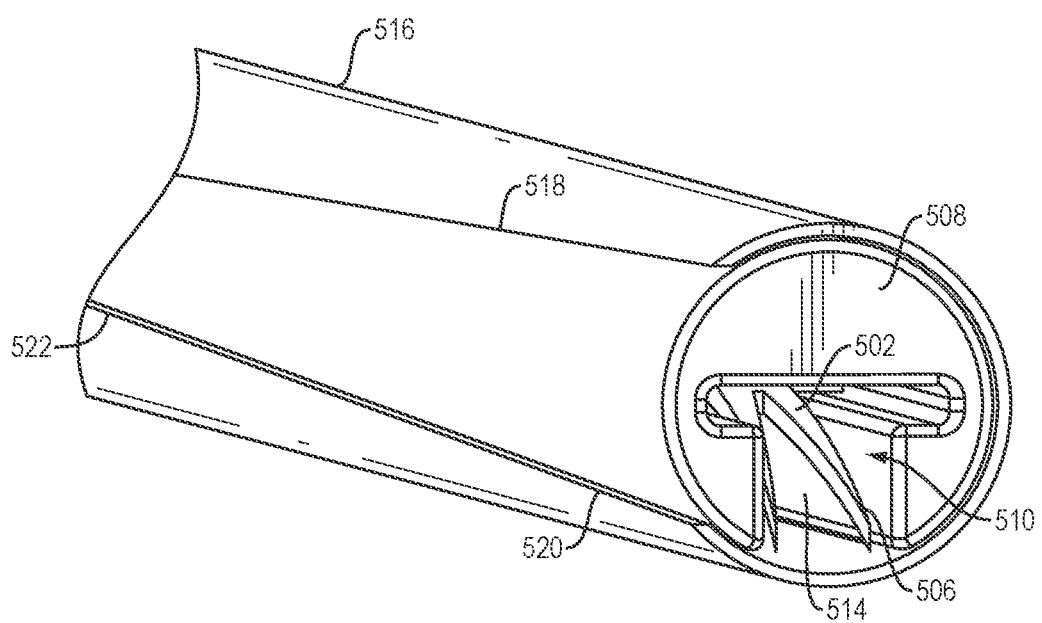
FIG. 5 is an illustration of a system with a slot along an outer sheath with a width of the slot wider at the distal end than at the proximal end of the slot according to an embodiment of the present disclosure.

An embodiment of a tissue retraction system of the present disclosure as illustrated in FIG. 5, may include a slot 518 that runs along a longitudinal axis of an outer sheath 516 with a wider portion at a distal end of the outer sheath 516 that tapers down to a narrower end 522 of the slot 518 at a proximal portion of the outer sheath 516. The wider end 520 of the slot 518 may be wider than an end 506 of the elongate flexible element 502 (and/or wider than a second portion 514 of the lumen 510 of the inner tubular element 508), while the narrow end 522 of slot 518 may be just wide enough to accommodate the end 506 of the elongate flexible element 502 (and/or as wide as the second portion 514 of the lumen 510). A medical professional may place the elongate flexible element 502 within an inner tubular element 508 and within the outer sheath 516, such that the distal end 506 of the elongate flexible element 502 is in close proximity to a first portion of target tissue and rotate and/or slide the outer sheath 516 with respect to the inner tubular element 508. Since the distal end 520 of the slot 518 is wider than at the proximal end 522, the distal end portion 506 of the elongate flexible element 502 will release from the distal end 520 of the slot 518 before the proximal end portion 506 at the narrow end 522 of the slot 518. In this position, the distal end 506 of the elongate flexible element 502 will deploy and engage the first portion of the target tissue, while the proximal end of the elongate flexible element 502 will still be constrained by the outer sheath 516. In this position, the medical professional may position the proximal end of the elongate flexible element 502 in close proximity to a second portion of the target tissue. The medical professional may then continue rotating and/or sliding the outer sheath 516 such that the narrow end 522 of the slot 518 matches with the proximal end of the elongate flexible element 502, or the proximal end reaches the wider end 520 of the slot 518 (in the case of sliding), releasing it into the second portion of the target tissue.

Figure 6A:
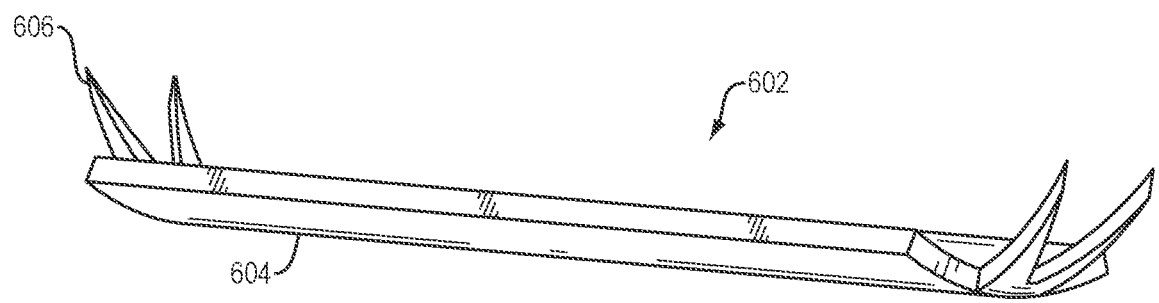
FIG. 6A is an illustration of an elongate flexible element as a bistable spring in a substantially planar configuration according to an embodiment of the present disclosure.
Figure 6B:
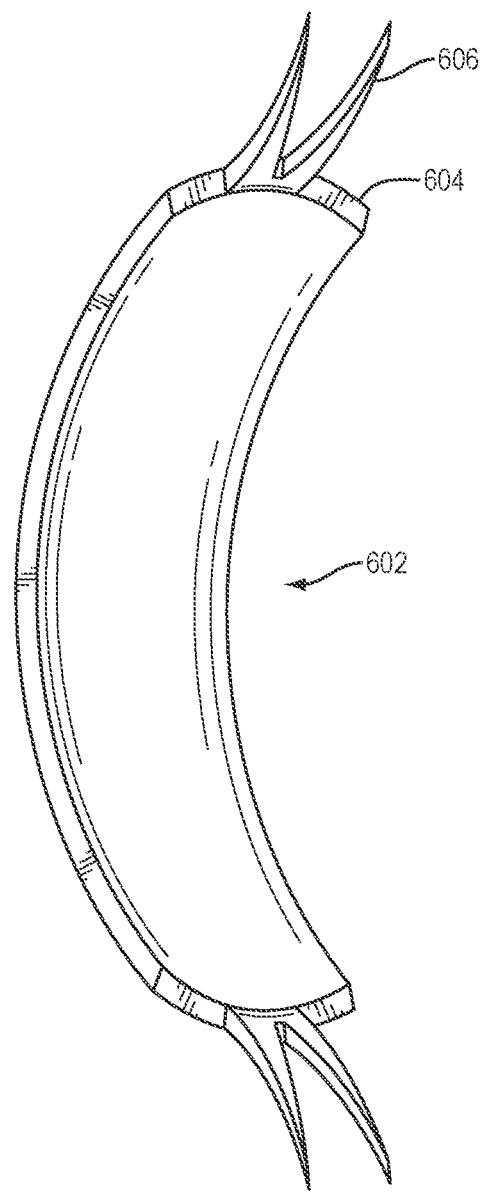
FIG. 6B is an illustration of the elongate flexible element of FIG. 6A in a substantially bowed configuration.
Figure 6C:
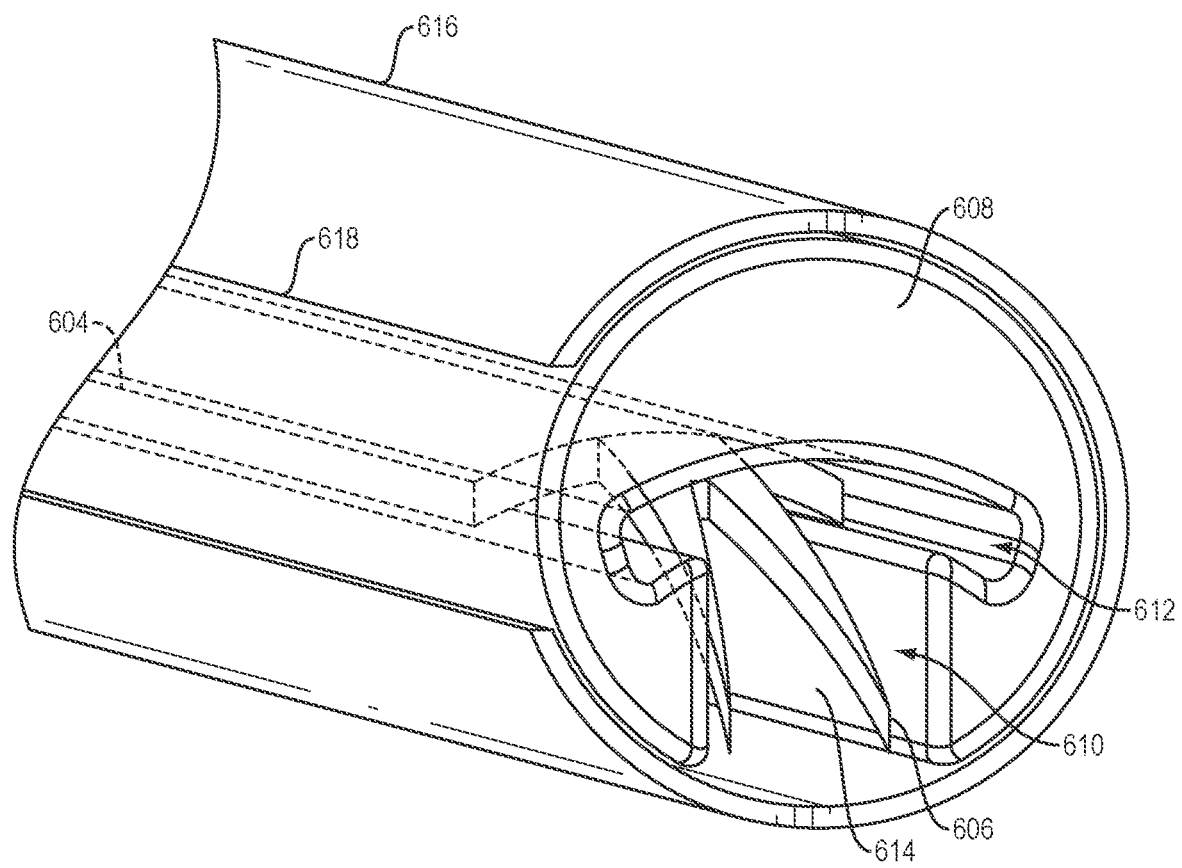
FIG. 6C is an illustration of the elongate flexible element of FIGS. 6A and 6B within a delivery catheter.
Figure 7A:
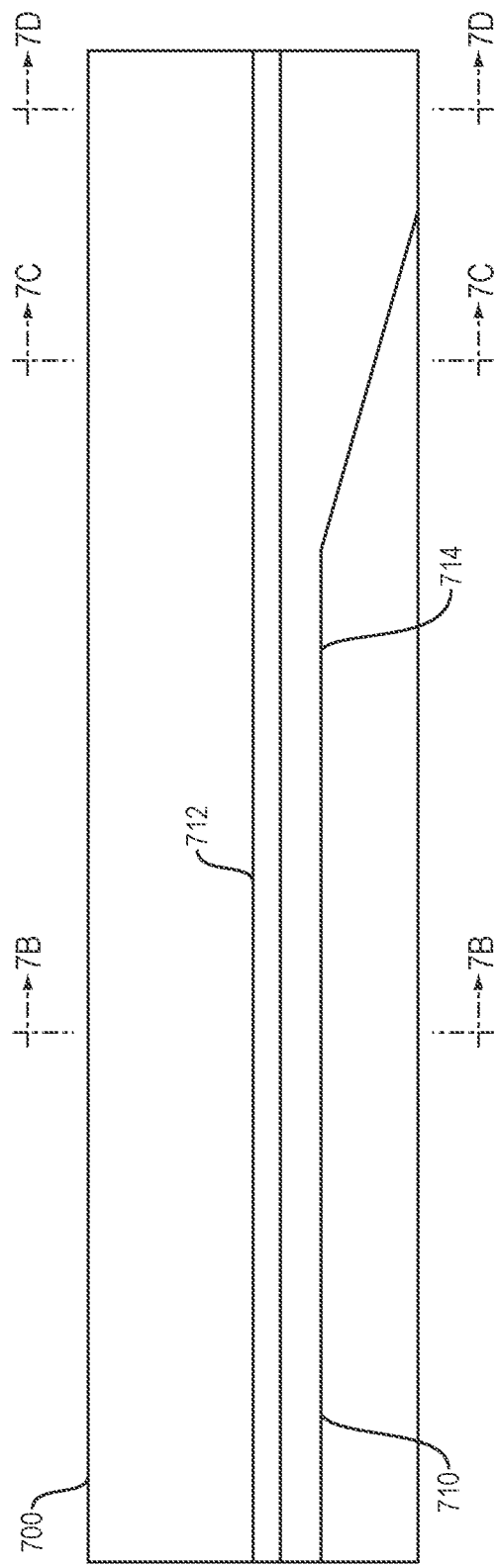
FIG. 7A is an illustration of a side view cross-section of an inner tubular element with a varying cross-section lumen according to an embodiment of the present disclosure.
Figure 7D:
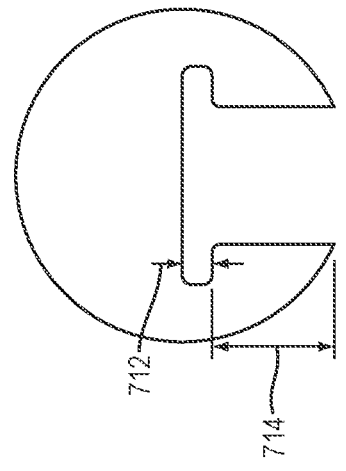
FIG. 7D is an illustration of a cross-section of 7A at the cross-section 7D.
Figure 7C:
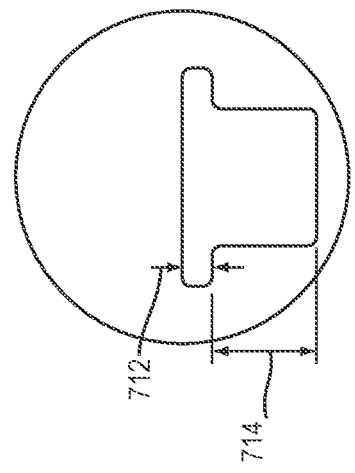
FIG. 7C is an illustration of a cross-section of 7A at the cross-section 7C.
Figure 7B:
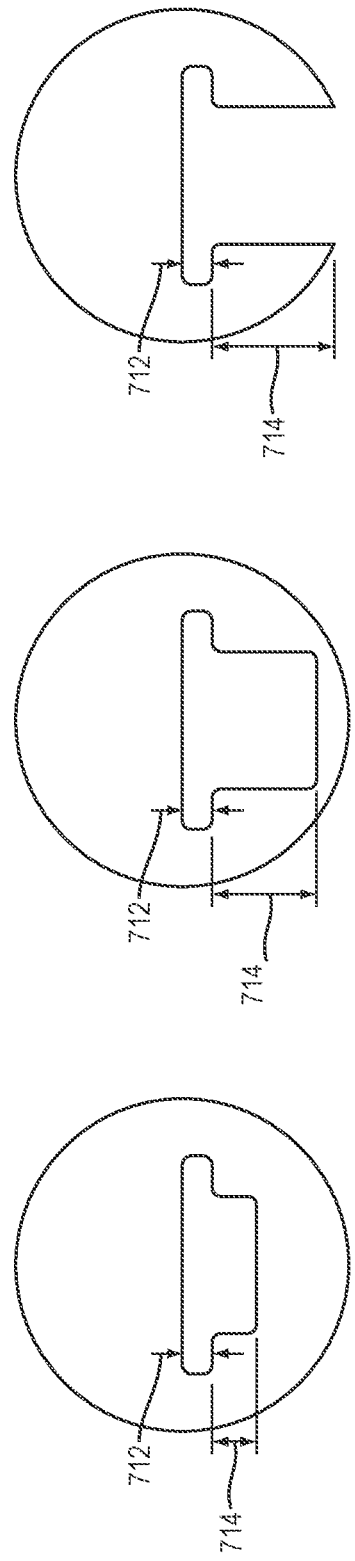
FIG. 7B is an illustration of a cross-section of 7A at the cross-section 7B.

An embodiment of a tissue retractor system as illustrated in FIGS. 6A-6C includes an elongate flexible element 602 that is a bistable spring. Such an elongate flexible element 602 may have two configurations. A substantially planar configuration of the elongate flexible element 602 is illustrated in FIG. 6A with a cross-section of the body 604 that is bowed radially in a first direction while the body 604 is straight along a longitudinal axis of the body 604. A bowed configuration of the elongate flexible element 602 is illustrated in FIG. 6B with a cross-section of the body 604 that is bowed radially in a second direction that is opposite the first direction, while the body 604 is longitudinally bowed. Distal and proximal ends 606 of the elongate flexible element 602 are configured to engage a target tissue. A body 604 of the elongate flexible element 602 is wider than the ends 606. The body 604 in this embodiment has curved sides that extend in a radial direction from a longitudinal axis, and does not need to be constrained in the substantially planar configuration in FIG. 6A. Once the elongate flexible element 602 is in position with the ends 606 engaged in the target tissue, a longitudinally perpendicular (i.e., radial force) may be applied to the elongate flexible element 602 in the substantially planer configuration of FIG. 6A to transition it to the bowed configuration of FIG. 6B.

With reference to FIG. 6C, the embodiment of the elongate flexible element 602 of FIGS. 6A and 6B may be disposed within a lumen 610 of an inner tubular element 608 in a substantially planar configuration of FIG. 6A. The body 604 of the elongate flexible element 602 may be slidingly disposed within a first portion 612 of the lumen, while the ends 606 of the elongate flexible element 602 may be slidingly disposed within a second portion 614 and constrained by an inner wall of the outer sheath 616. A slot 618 on the outer sheath 616 may be rotated and/or slid to provide a pathway at least partially lined up with the second portion 614 of the lumen 610 for the end portions 606 of elongate flexible element 602 to deploy. The profile of the first portion 612 may be shaped to match the profile of the elongated flexible element 602.

An embodiment of a tissue retraction device of the present disclosure is illustrated in FIGS. 7A-7D and may include a tubular element 700 with a lumen 710 therethrough that may slidingly accommodate an elongate flexible element of the disclosure. A body portion of the elongate flexible element may be disposed within a wider first portion 712 of the lumen 710 while the ends of the elongate flexible element may be disposed within a narrower second portion 714 of the lumen 710. The first portion 712 remains uniform throughout the lumen 710, while the second portion 714 maintains a short cross-section depth at the proximal end of the tubular element 700 (FIG. 7B) that transitions into a taller cross-section (FIG. 7C) towards a distal end of the tubular element 700. A most distal section of the lumen 710 has a cross-section (FIG. 7D) with a second portion 714 that is open to the perimeter of the tubular element 700. An elongate flexible element with ends configured to engage tissue may be slidingly disposed in the lumen 710 constrained within the second portion 714. Translating the elongate flexible element proximally through the lumen 710 (e.g., through the use of a push member) subjects the distal end of the elongate flexible element to the transitioning cross-section of the lumen 710, e.g., FIG. 7C, where the second portion 714 becomes taller to initiate the deployment of the ends of the elongate flexible element. As an end of the elongate flexible element configured to engage a target tissue translates within the second portion 714 of the lumen 710 from a short cross-section, e.g., at FIG. 7B, to a taller cross-section that is open to the perimeter of the tubular element 700, e.g., at FIG. 7D, the elongate flexible element becomes unconstrained and deploys at the distal end of the tubular element 700 into a first portion of a target tissue. The elongate flexible element may continue to be pushed distally out of the tubular element 700 such that the distal end also unconstrains and deploys from the second portion 714 of the lumen and into a second portion of the target tissue as the elongate flexible element translates from the proximal end to the distal end of the lumen 710. Alternatively, a lumen 710 could have no transitional cross-section as in FIG. 7C, transitioning abruptly from FIG. 7B to FIG. 7D. Additionally, while a substantially T-shaped cross-section of a lumen 710 is illustrated in FIGS. 7A-7D, the cross-section may instead take on a substantially C-shaped cross-section such as that illustrated in FIG. 4B that transitions from a shorter "D-shape" at a proximal portion of the inner tubular element 700 to the C-shape at a distal portion of the inner tubular element 700.

Figure 8A:
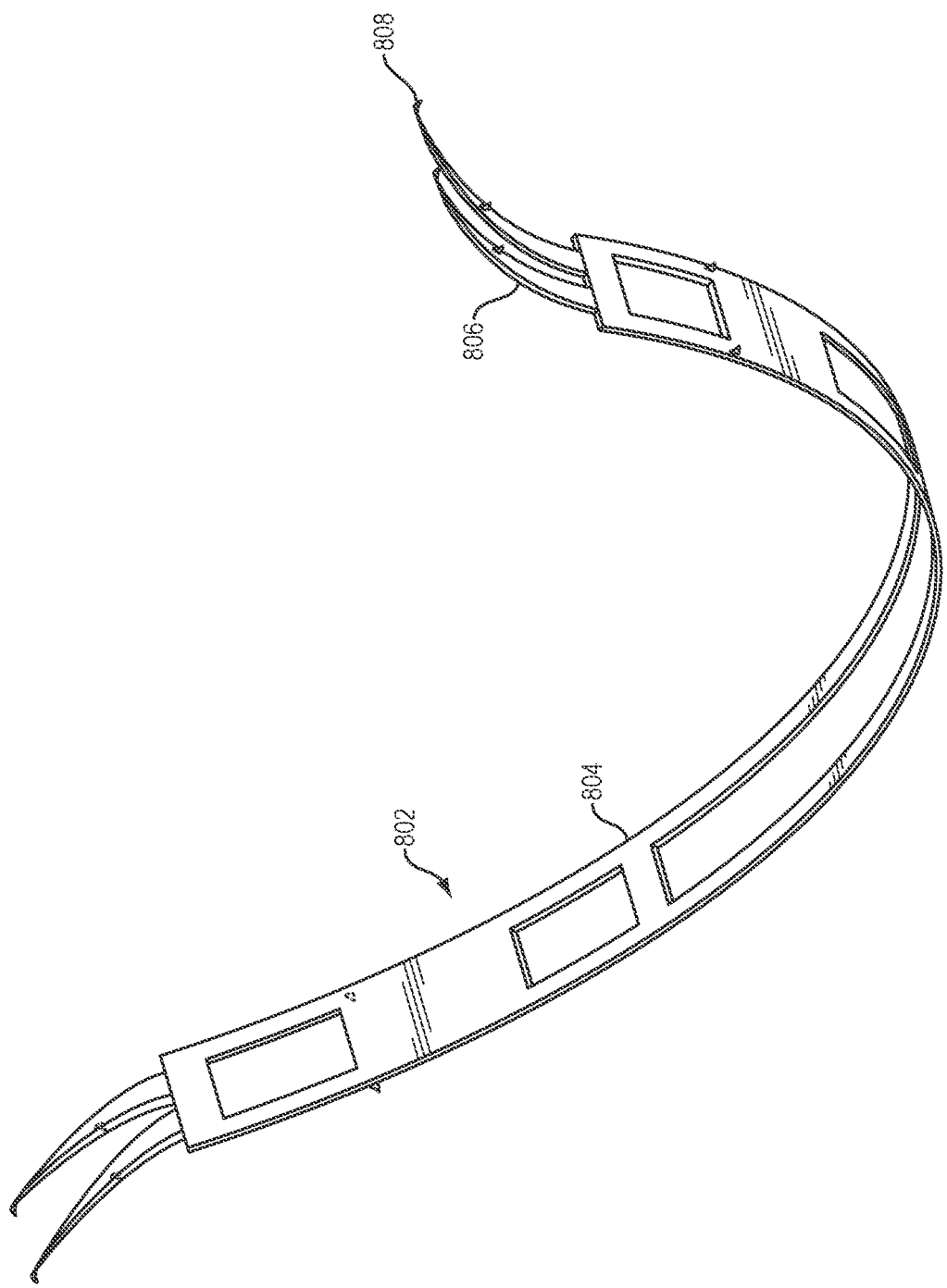
FIG. 8A is an illustration of an elongate flexible element with barbs according to an embodiment of the present disclosure.
Figure 8B:
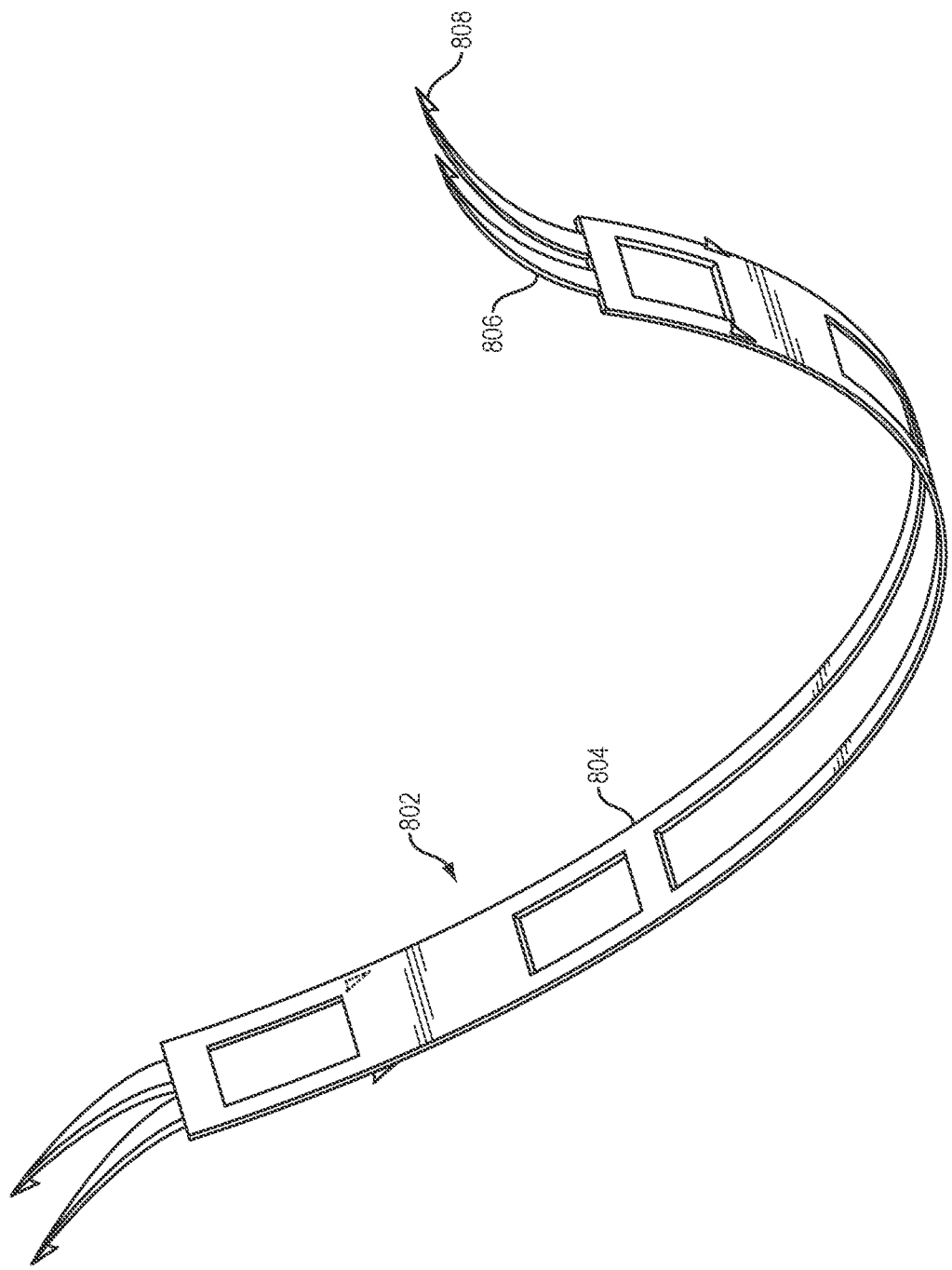
FIG. 8B is an illustration of an elongate flexible element with hooks according to an embodiment of the present disclosure.
Figure 8D:
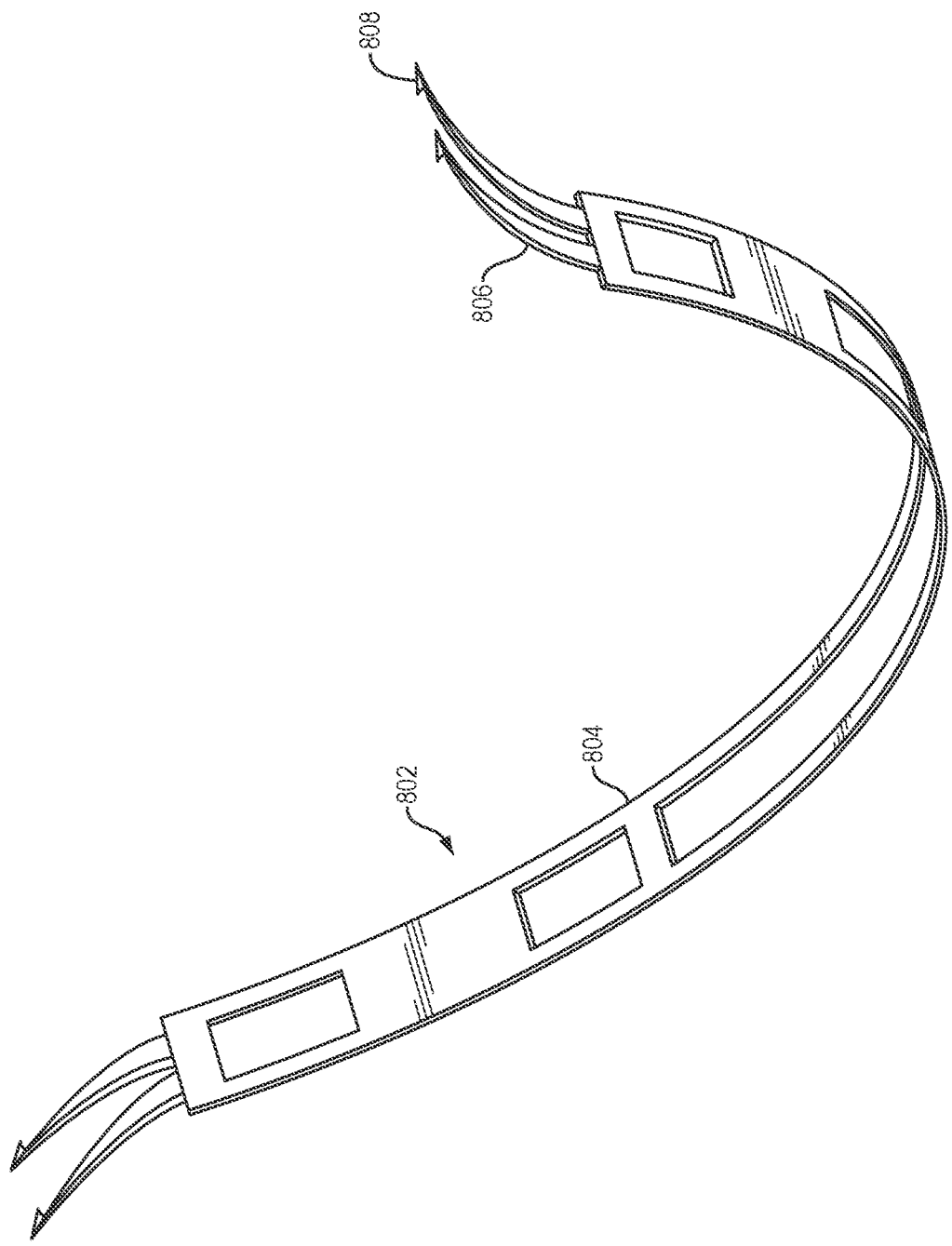
FIG. 8D is an illustration of an elongate flexible element with hooks according to an embodiment of the present disclosure.

Embodiments of an elongate flexible element may include a multitude of mechanisms configured to engage tissue and prevent the elongate flexible element from disengaging or twisting away from the target tissue. FIGS. 8A through 8D illustrate some examples. These mechanisms may be disposed along the end portions 806 of the elongate flexible element 802 and/or along the body portion 804 to assist in tissue engagement. The tissue engagement mechanisms may engage tissue separately or together as the end portions 806 also engage tissue, and/or when the body portion 804 comes into proximity of tissue. FIG. 8A illustrates barbs 808 along the elongate flexible element 802, including barbs 808 at the tips of the end portions 806 pointed in one direction while other barbs 808 on the end portions 806 not at the tips are pointed in the opposite direction. Additionally, barbs 808 are illustrated along the body portion 804. FIG. 8B illustrates hooks 808 along one side of the elongate flexible element 802 on the end portions 806 and on the body portion. The hooks 808 may easily pierce target tissue, allowing for the wider portion of the sharp ends to engage the target tissue as the hooks 808 are pushed deeper into the target tissue, while a second sharp end at the opposing wider portion makes it difficult to un-embed the hook 808 from the target tissue. FIG. 8C illustrates double-sided hooks 808 on the end portions 806 of the elongate flexible element 802 providing more sharp edges to pierce and embed into the target tissue. FIG. 8D illustrates hooks 808 on an opposing surface of the end portions 806 of the elongate flexible element 802 than those illustrated in FIG. 8B. These hooks and barbs, in various combinations, configurations and orientations, may be utilized according to the desired tissue effect with any of the elongate flexible elements of the present disclosure.

Figure 9A:
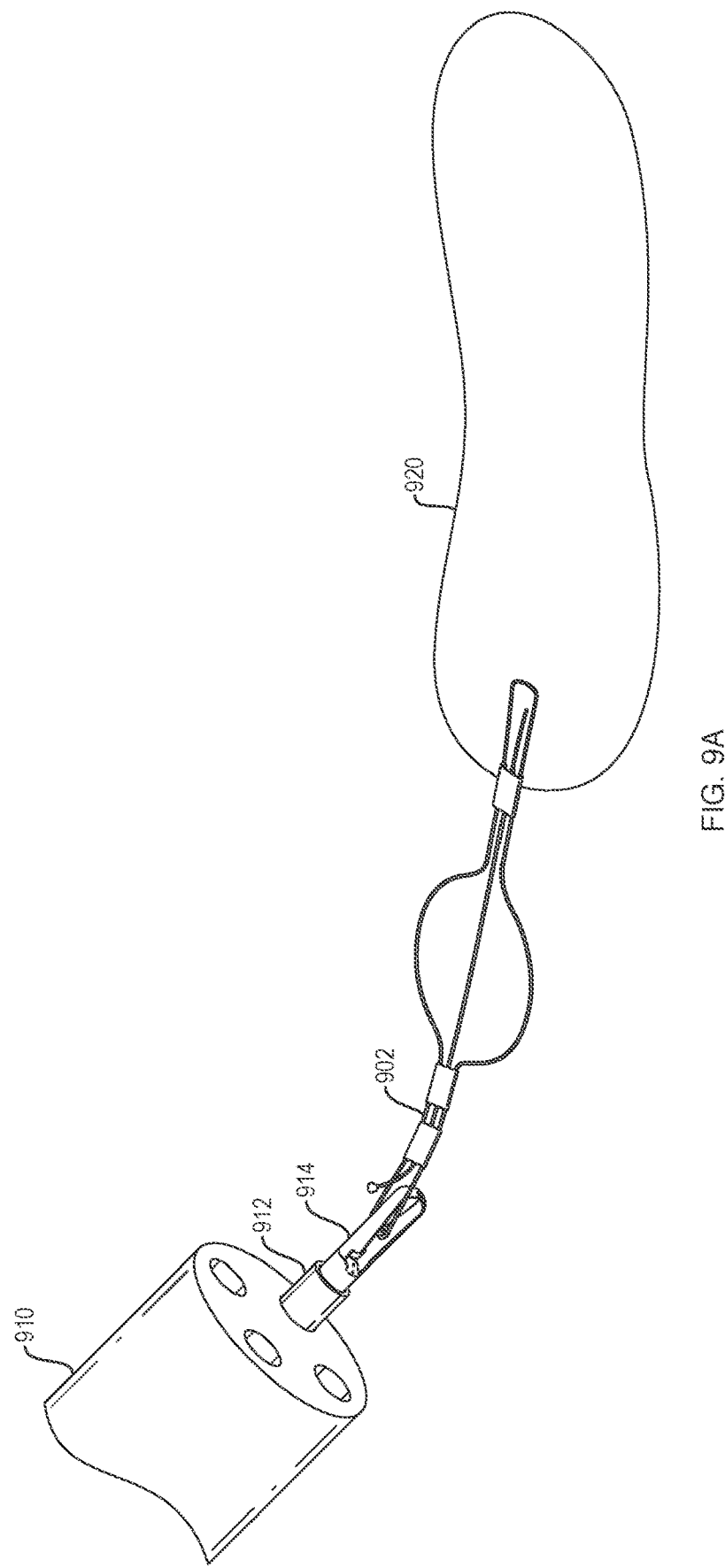
FIG. 9A is an illustration of a system being deployed according to an embodiment of the present disclosure.

In one embodiment, the present disclosure provides a tissue retraction system as illustrated in FIG. 9A using an endoscope 910 to deliver and position a delivery catheter 912 containing at least one tissue fastener 914 carrying an elongate flexible element 902 towards the site of the target tissue 920.

Figure 9B:
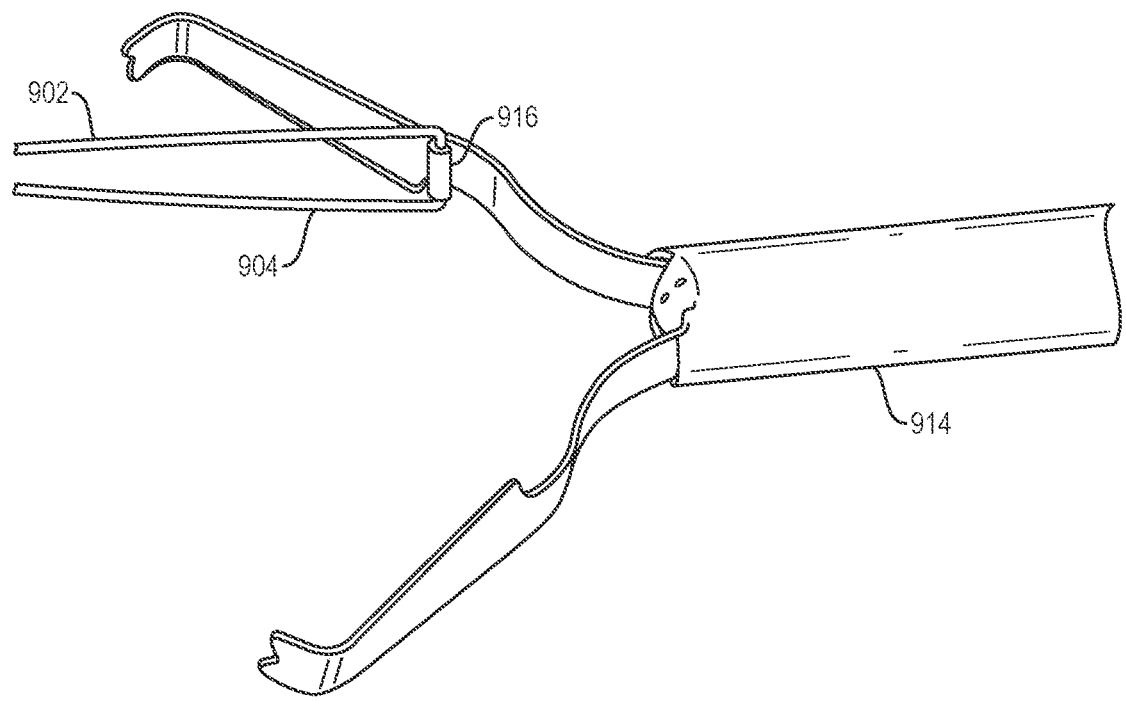
FIG. 9B is an illustration of the system embodiment of FIG. 9A with a loop at an end of an elongate flexible element being engaged by a tissue fastener.

An embodiment of the elongate flexible element 902 may include ends configured to be engaged by a tissue fastener 914 as illustrated in FIG. 9B. In FIG. 9B, these ends include loops 904 that may be engaged by a hook 916 on the tissue fastener 914. The length of the loops 904 may be such that the tissue fastener 914 may readily be manipulated (e.g., rotated, flipped, etc.) while still engaging the loop 904. Although the loop 904 is illustrated as a closed loop, it may instead be other shapes such as, for example, an arm or a hook. Although both ends are each illustrated with a loop 904, one end could have a loop 904 while the other could have a pre-attached tissue fastener 914 without a loop.

Figure 9C:
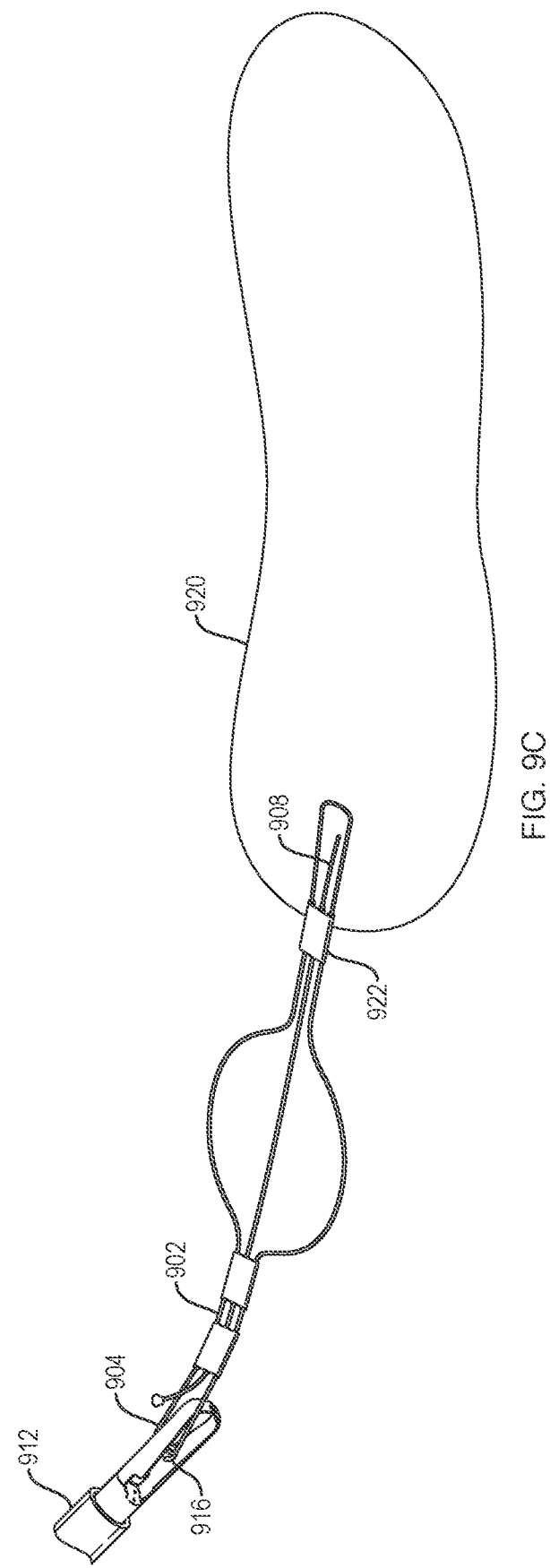
FIG. 9C is an illustration of the system of FIGS. 9A and 9B with the elongate flexible element and a tissue fastener being deployed.

Referring to FIG. 9C, the system of FIGS. 9A and 9B may be introduced to the target tissue site by engaging a proximal loop 904 with a tissue anchor 914 (engaged with a hook 916 in this embodiment) and loading the elongate flexible element 902 looped to the tissue fastener 914 into a delivery catheter 912. The loops 904 can be different shapes and the hooks 916 may be configured in different ways, so long as the tissue fastener 914 can engage and secure the elongate flexible element 902 to the target tissue site. The elongate flexible element 902 has a bowed configuration along its longitudinal axis when unconstrained. A substantially straight control wire 908 is disposed within a lumen created by guide members 922 along the elongate flexible element 902, whereby the control wire while deployed through the lumen of the guide members constrains the elongate flexible element 902 in a substantially planar configuration. The control wire 908 may comprise a stiffer material and/or a larger thickness than the material and/or thickness of the rest of the elongate flexible element 902. Although the guide members 922 with lumens for the control wire are depicted as flattened and rectangular, it should be appreciated that they may take on a multitude of shapes such as, for example, circular, semi-circular, oval, square, a hybrid of shapes, etc. Also, the elongate flexible element 902 may include a variety of constrained configuration lengths (e.g., approximately 6.0 inches (approximately 152 mm); approximately 5.0 inches (approximately 127 mm); approximately 4.0 inches (approximately 101.6 mm); approximately 3.0 inches (approximately 76.2 mm); approximately 2.75 inches (approximately 69.85 mm); approximately 2.0 inches (approximately 50.8 mm); approximately 1.5 inches (approximately 38.1 mm); approximately 1.0 inch (approximately 25.4 mm)). To set up the system for delivery, the distal end of the elongate flexible element 902 that is not engaged by a tissue fastener 914 may be loaded into the delivery catheter 912 first such that the distal end is distal to the tissue fastener 914 that it is connected to the elongate flexible element at the proximal end. As such, the proximal end follows behind the rest of the elongate flexible element 902 in the delivery catheter 912. A flexible bow portion 906 (a pair of elements extending substantially away from each other in a longitudinal plane in an expanded configuration in this embodiment) transitions to a collapsed configuration while constrained within the delivery catheter. The tissue fastener 914 may be translated distally while in the delivery catheter 912, which also pushes the elongate flexible element 902 distally through the delivery catheter 912.

Alternatively, the tissue fastener 914 could be loaded into the deliver catheter 912 distally to the elongate flexible element 902. In this alternative embodiment setup, the tissue fastener 914 would pull the elongate flexible element 902 distally as the tissue fastener is translated distally. As illustrated in the embodiment of FIG. 9C, the tissue fastener may translate the elongate flexible element 902 out of the delivery catheter by pushing it distally. Once the bow portion 906 has exited the delivery catheter, it no longer is constrained in the collapsed configuration and may expand to the expanded configuration. Since the elongate flexible element 902 is engaged by the hook 916 of the tissue fastener 914 at the proximal loop 904, movement of the tissue fastener 914 controls movement of the elongate flexible element 902. The elongate flexible element 902 may be maneuvered toward the target tissue 920.

Figure 9D:
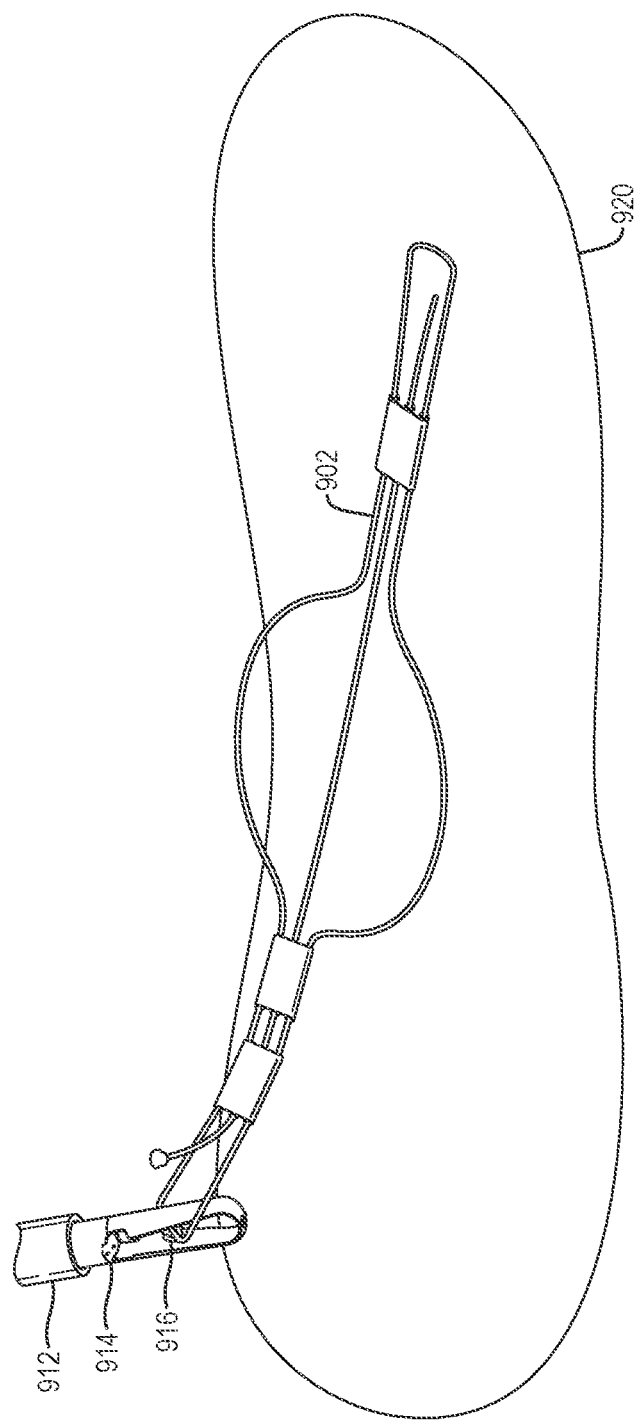
FIG. 9D is an illustration of the system of FIGS. 9A-9C with the elongate flexible element being translated into position over a target tissue.

Referring to FIG. 9D, the tissue retractor system illustrated in FIG. 9C may translate the elongate flexible element 902 over the target tissue after it exits the catheter by translating the tissue fastener 914 engaged at the proximal end of the flexible element 902 toward a proximal portion of the target tissue 920. The tissue fastener 914 engaging the proximal end of the elongate flexible element 902 is then able to be fastened to the proximal portion of the target tissue 920. The fastener 914 is freely rotatable even when attached to the elongate flexible element 902 in order to best position the fastener 914 to engage the target tissue 920 and position the elongate flexible element 902 across the target tissue 920. When the tissue fastener 914 is fastened to the target tissue 920, a distal end of the elongate flexible element 902 is free-hanging, but also in proximity to the desired location on the target tissue 920 (e.g. a distal portion of the target tissue) for tissue retraction.

Figure 9E:
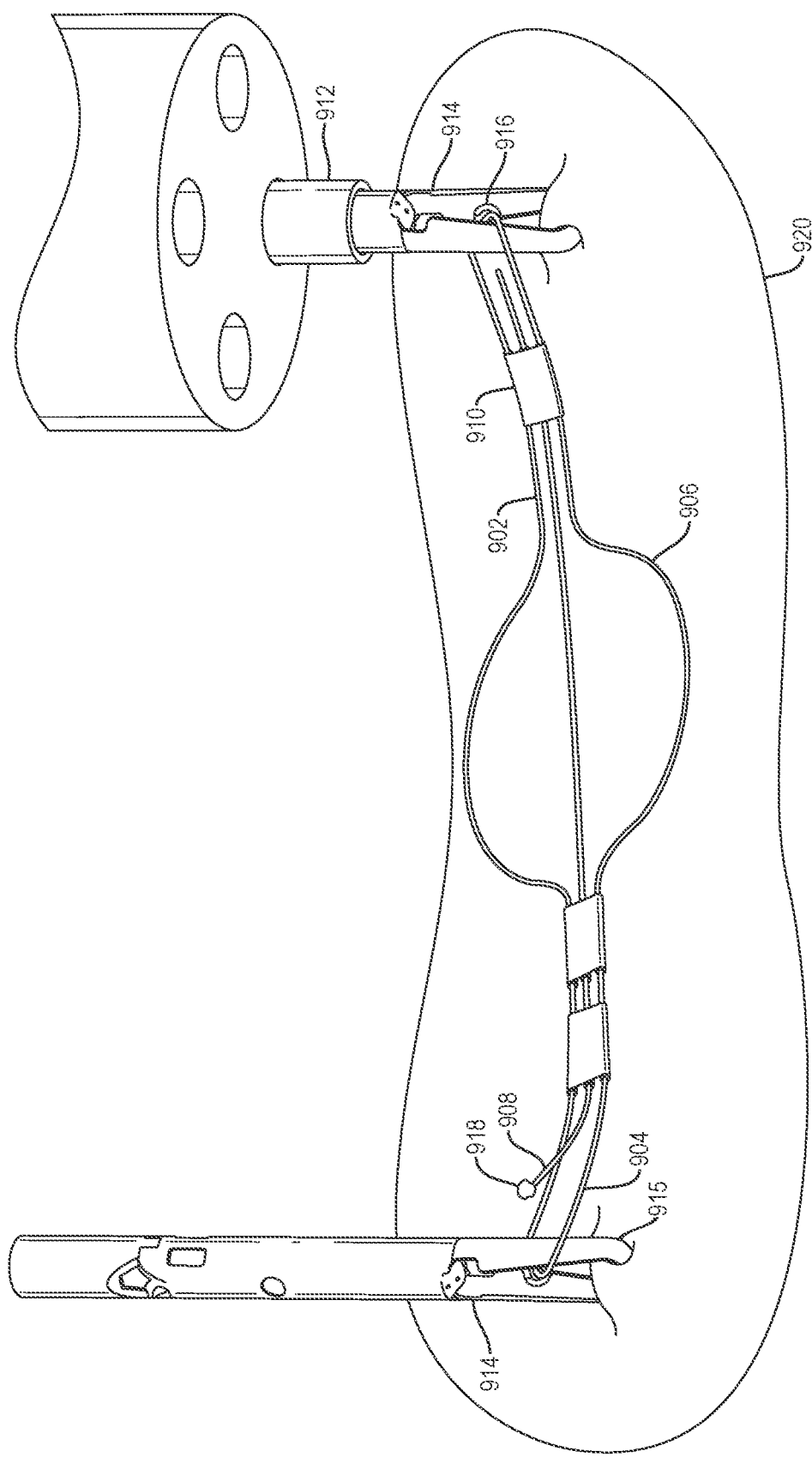
FIG. 9E is an illustration of the system of FIGS. 9A-9D with a second tissue fastener engaging a loop of the elongate flexible element and also engaging the target tissue.

Referring to FIG. 9E, the tissue retractor system of FIGS. 9A-9D may introduce an additional tissue fastener 914 to engage a distal loop 904 of the elongate flexible element 902. A medical professional may introduce the additional tissue fastener 914 by using a delivery catheter 912 through the working channel of an endoscope. Alternatively, the same delivery catheter may be reloaded with a new fastener 914 and/or a separate delivery catheter 912 may be used. The tissue fastener 914 may include a hook 916 to engage the distal loop 904. The delivery catheter 912 and tissue fastener 914 may be modeled, as an example, along the lines of the RESOLUTION™ clip devices sold by Boston Scientific Corporation. Variations on these devices and other devices, and associated components and features which may be suitable for the devices and fasteners of the present disclosure, can be found in U.S. application Ser. No. 14/701,157

(US2015023080A1) and Ser. No. 13/463,560 (US20130123807A1), the entire disclosures of which are incorporated by reference herein in their entirety. The fastener may be deployed to engage the loop 904 by the hook 916 before being locked into position in the target tissue 920. The tissue fasteners 914 are able to be disengaged from the delivery catheter 912 and left behind with the elongate flexible element 902. To aid in manipulating the elongate flexible element 902, the loops 904 may be larger than a tissue-grasping portion 915 of the tissue fastener 914 such that they can flip to the opposite side of the tissue fastener 914 when a medical professional is positioning the elongate flexible element 902.

A control wire 908 may include a visual marker 918 that may easily be seen by the medical professional to indicate the position of the control wire 908 and the proximal end portion of the elongate flexible element 902. The marker may be a colored body disposed on the control wire 908, a radiopaque material such that it shows up on a fluoroscope, or may be a mark made into the control wire 908 (e.g., scratched, etched, indented, laser-etched, etc.). The control wire 908 may have its proximal end bent away from the elongate flexible element 902 such that the marker 918 is unobstructed for even more visibility. This bending of the control wire 908 also assists in grasping of the control wire 908 for removal. The marker may have an expanded profile compared to the rest of the control, e.g., spherical, so as to be more easily grasped by a tool inserted through the catheter and/or scope in order to remove the control wire from the elongate element.

Figure 9F:
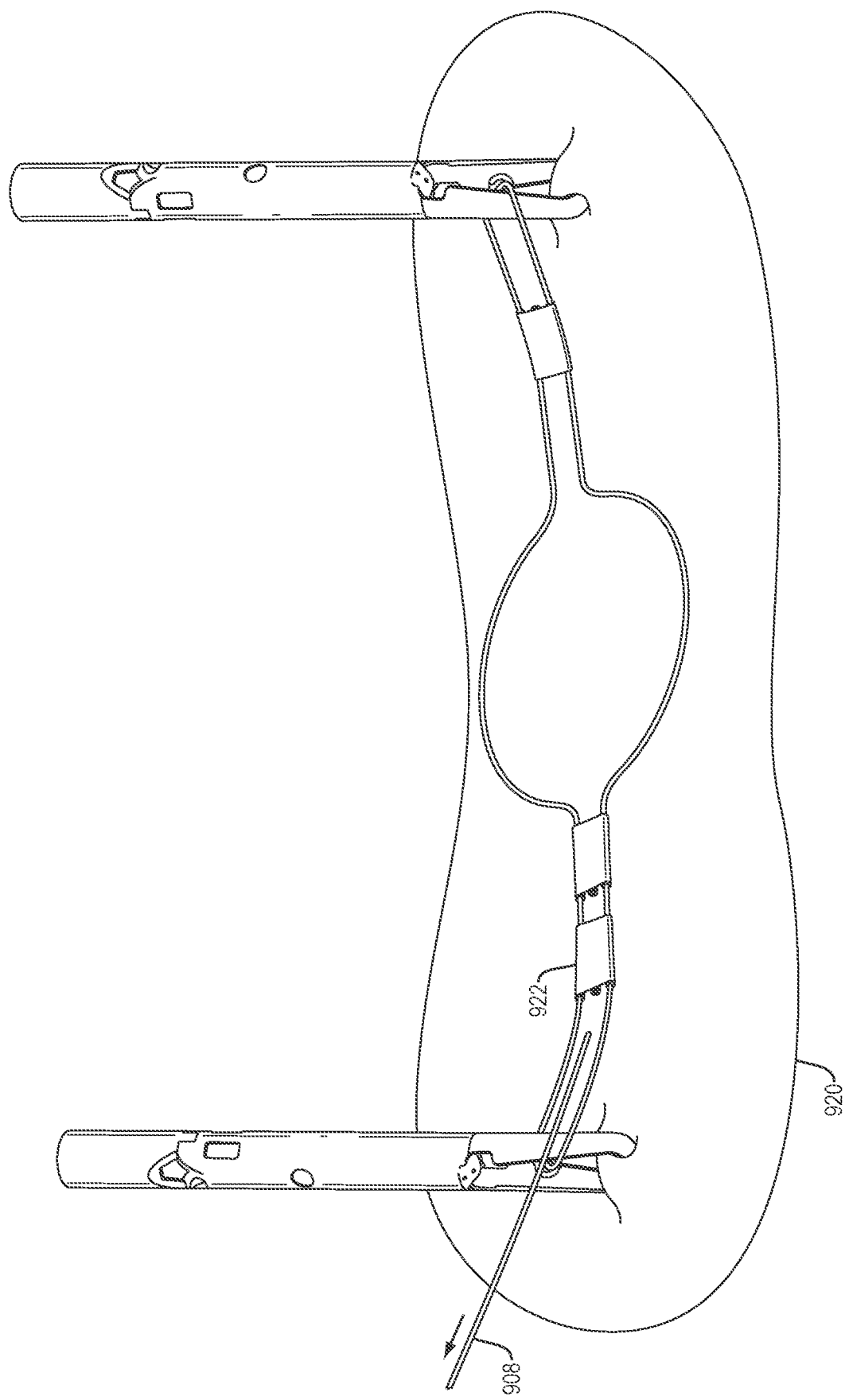
FIG. 9F is an illustration of the system of FIGS. 9A-9E with a control wire being removed.

Once the second tissue fastener 914 is engaged to the distal loop 904, the tissue fastener 914 may be manipulated (e.g., rotated, flipped, etc.) to position the elongate flexible element 902 as desired along the target tissue 920. Once the elongate flexible element 902 is in position, the additional tissue fastener may engage a second portion (e.g. a distal portion) of the target tissue 920, thereby securing the elongate flexible element 902 to the target tissue. The delivery catheter 912 may then release the second tissue fastener 914. The medical professional may transition the elongate flexible element 902 into its bowed configuration along its longitudinal axis prior to dissecting the target tissue. This may allow for partial tissue retracting during the dissection process. Alternatively, the elongate flexible element 902 may be left in its substantially planar configuration prior to and/or during dissecting of the target tissue. To transition the elongate flexible element 902 into the bowed configuration, a grasping device may be introduced to the site of the target tissue 920. The grasping device may be maneuvered toward the marker 918 on the bent portion of the control wire 908. Referring to FIG. 9F, the control wire 908 may be grasped and pulled out of the guide members 922. Without the control wire 908, the elongate flexible element 902 may transition from the substantially planar configuration to a bowed configuration along its longitudinal axis, initiating retraction forces on the target tissue 920.

Figure 9G:
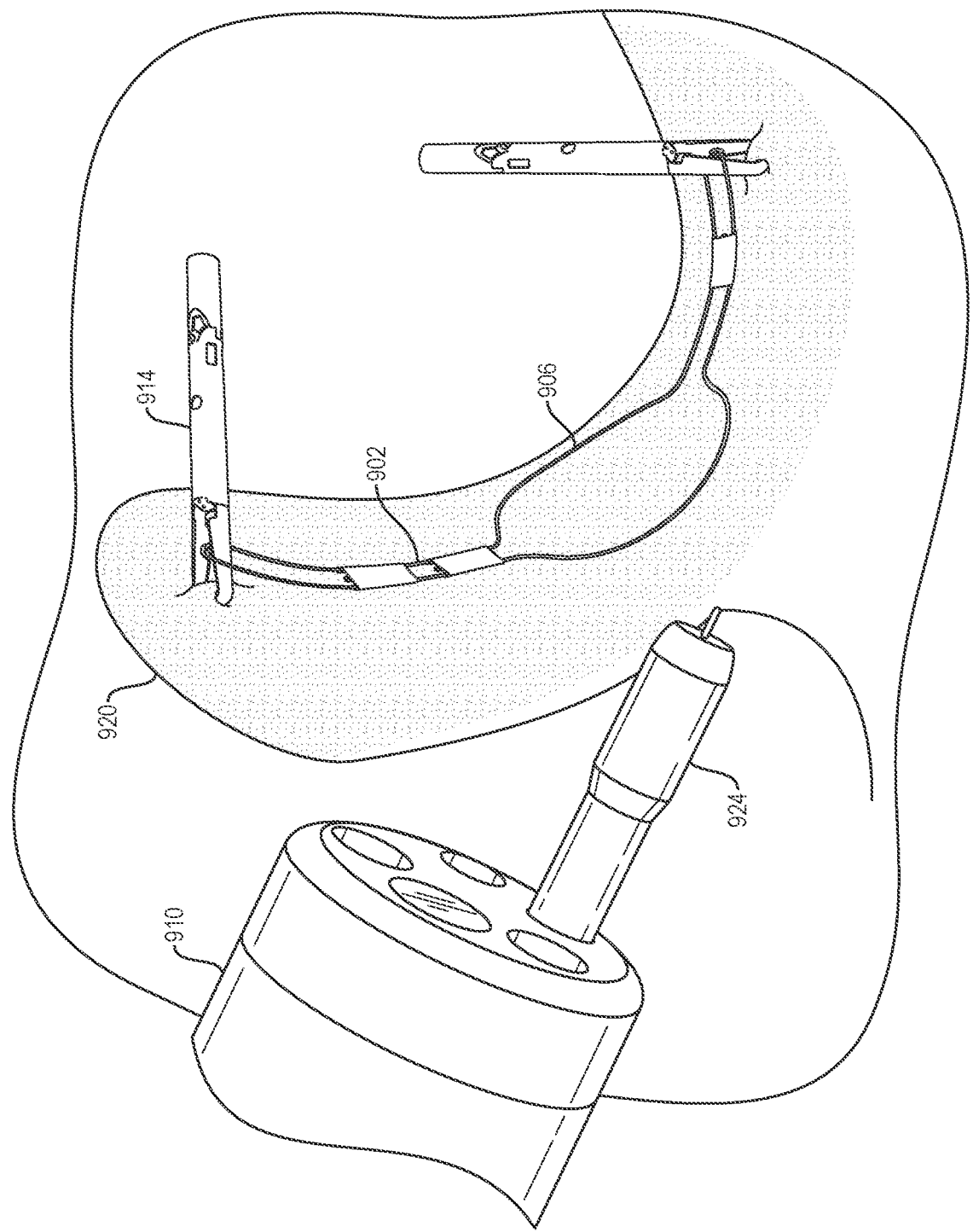
FIG. 9G is an illustration of the system of FIGS. 9A-9F with a dissecting element removing the target tissue to be dissected.

Referring to FIG. 9G, the system of FIGS. 9A-9F is illustrated with the control wire 908 of the elongate flexible element 902 removed such that the elongate flexible element 902 is in the bowed configuration. In this configuration, the elongate flexible element 902 subjects a retraction force upon each of the tissue fasteners 914 and therefore also on the target tissue 920. A dissecting device 924 may be introduced through the working channel of an endoscope 910 to dissect a perimeter around the target tissue 920. This dissection of the target tissue 920 releases the target tissue 920 from the surrounding tissue, allowing the target tissue 920 to succumb to the retraction forces of the elongate flexible element 902 in the bowed configuration. While distal and proximal ends of the target tissue 920 are illustrated as being lifted by the fasteners 914 and loops 904, additional arms may extend off of the elongate flexible element 902 in directions (such as normal to the elongate flexible element) that may extend across the target tissue 920 and include a loop 904 that may be engaged by a hook 916 on a tissue fastener 914. A bowed portion 906 may extend outwards radially from the longitudinal axis in a plane substantially parallel with the target tissue. As the target tissue 920 begins to retract from the surrounding tissue, the bowed portion 906 may provide additional surface area and resistance to side portions of the target tissue 920 retracting and folding over the elongate flexible element 902. A complete dissection around the perimeter of the target tissue 920 will sever it from the surround tissue, allowing the elongate flexible element 902 to fully lift and retract the dissected target tissue 920 from the surrounding tissue. The target tissue 920 and the tissue retraction system may be removed from the body by a medical professional, or left in the body to be passed through the G.I. tract.

In the first substantially planar or flat configuration of any of the embodiments, the elongate flexible element may have a portion or all of its body placed in contact with the tissue surface. In one embodiment, the elongate flexible element may include a width and a thickness, wherein the width exceeds the thickness such that the elongate flexible element resists the tendency to roll or twist during a dissection procedure. For example, the elongate flexible element may include a width (e.g., approximately 0.070 inches (approximately 1.778 mm); approximately 0.065 inches (approximately 1.651 mm); approximately 0.060 inches (approximately 1.524 mm); approximately 0.055 inches (approximately 1.397 mm); approximately 0.050 inches (approximately 1.27 mm)) that is greater than the thickness (e.g., approximately 0.040 inches (approximately 1.016 mm); approximately 0.035 inches (approximately 0.889 mm); approximately 0.030 inches (approximately 0.762 mm); approximately 0.025 inches (approximately 0.635 mm); approximately 0.020 inches (approximately 0.508 mm)), in some cases the width may be as much as approximately two times greater than the thickness. The elongate flexible element may be made, for example, from a variety of resilient biocompatible materials, including metals and metal alloys such as platinum, tungsten, titanium, stainless steel, nickel and nickel-titanium alloys (e.g., nitinol), polymers such as acrylate-based polymers, polyurethane-based polymers, polynorbornene-based polymers, and polylactide-based polymers, and any combinations thereof.

It should be appreciated that the "force" stored within such materials when in the constrained configuration allows the elongate flexible element to apply and maintain upward lifting/retraction pressure against the tissue in which it is embedded. The natural tendency of the elongate flexible element to move (i.e., return) from the flat or planar shape of the first configuration, to the bowed (e.g., round or hemispherical) shape of the second configuration allows the dissected portions of the target tissue to be lifted or elevated above the dissecting plane such that the non-dissected target tissue portion may be more easily visualized and more efficiently excised. The shape of the second configuration may be controlled during manufacturing the elongate flexible element so as to impart or set a desired memory in the elongate flexible element material that is assumed in the relaxed, unconstrained position.

A method for retracting dissected tissue may involve a medical professional advancing a delivery catheter through a working channel of an endoscope to a position adjacent to a target tissue such that a distal end of the delivery catheter is in proximity to a first portion of the target tissue. The medical professional may advance an elongate flexible element through a working channel of the delivery catheter such that a distal end of the elongate flexible element engages the first portion of the target tissue beyond the distal end of the delivery catheter. The medical professional may proximally retract the delivery catheter such that a proximal end of the elongate flexible element moves beyond the distal end of the delivery catheter. The medical professional may urge the distal end of the delivery catheter against the proximal end of the elongate flexible element such that the proximal end of the elongate flexible element engages a second portion of the target tissue. The medical professional may rotate and/or slide an outer sheath of the delivery catheter in relation to an inner tubular element of the delivery catheter releasing the distal end of the elongate flexible element into the first portion of target tissue and subsequently retracting the proximal end of the elongate flexible element into the second portion of the tissue. The medical professional may advance a tissue dissecting element through the working channel of the endoscope and dissect along a margin of the target tissue as the elongate flexible element moves from the first configuration to the second configuration.

Devices according to the embodiments described, and in accordance with other embodiments of the present disclosure, alone or in a system or kit or as part of a method or procedure, including with other accessories, may be used in cavities, lumens, tracts, vessels and organs of the body, etc.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. A tissue retractor system, comprising:
   a delivery catheter comprising:
      an inner tubular element with a lumen therethrough;
      an outer sheath disposed about the inner tubular element, the outer sheath and inner tubular element slidingly disposed relative to each other; and
   an elongate flexible element configured to transition between a first configuration when constrained and a second bowed configuration when unconstrained, the elongate flexible element disposed within the lumen of the inner tubular element, the elongate flexible element and inner tubular element slidingly disposed relative to each other and the outer sheath comprising:
      a distal end having an end width and configured to engage a first target tissue portion;
      a proximal end having an end width and configured to engage a second target tissue portion; and
      a body portion having a body width connecting the distal end to the proximal end,
   wherein the body width is wider than the end width of the distal end and proximal end;
   wherein the lumen has a cross-section that accommodates the body width and the end widths;
   wherein a first portion of the cross-section substantially matches the body width; and
   wherein a second portion of the cross-section substantially matches the end widths.

2. The system of claim 1, wherein the outer sheath has a slot, whereby rotating one or both of the outer sheath and the inner tubular element relative to each other to align the slot with the second portion of the cross-section allows at least one anchor of the distal end and the proximal end of the elongate flexible element to deploy radially outward from the outer sheath.

3. The system of claim 1, wherein the outer sheath has a slot, whereby sliding one or both of the outer sheath and the inner tubular element relative to each other to align the slot with the second portion of the cross-section allows at least one anchor of the distal end and the proximal end of the elongate flexible element to deploy radially outward from the outer sheath.

4. The system of claim 1, wherein the cross-section is substantially T-shaped and wherein the first portion of the cross-section is configured to slidingly accept the body portion of the elongate flexible element and the second portion of the cross-section is configured to slidingly accept the distal end and proximal end of the elongate flexible element.

5. The system of claim 1, wherein the cross-section is substantially C-shaped and wherein the first portion of the cross-section is configured to slidingly accept the body portion of the elongate flexible element and the second portion of the cross-section is configured to slidingly accept the distal end and proximal end of the elongate flexible element.

6. The system of claim 1, wherein the distal end and the proximal end each comprise one or more tissue anchors selected from the group consisting of tines, forks, hooks, fingers, barbs, loops and clips.

7. The system of claim 1, wherein the first portion remains uniform throughout the lumen, and wherein the second portion has a first height dimension at a proximal end of the inner tubular element that transitions into a second height dimension at a distal end of the inner tubular element, wherein the first height dimension is smaller than the second height dimension.

8. A tissue retractor system, comprising:
   a delivery catheter comprising:
      an inner tubular element with a lumen therethrough;
      an outer sheath disposed about the inner tubular element, the outer sheath and inner tubular element slidingly disposed relative to each other; and
   an elongate flexible element configured to transition between a first configuration when constrained and a second bowed configuration when unconstrained, the elongate flexible element disposed within the lumen of the inner tubular element, the elongate flexible element and inner tubular element slidingly disposed relative to each other and the outer sheath comprising:
      a distal end having an end width and configured to engage a first target tissue portion;
      a proximal end having an end width and configured to engage a second target tissue portion; and
      a body portion having a body width connecting the distal end to the proximal end,
   wherein the body width is wider than the end width of the distal end and proximal end;
   wherein the lumen has a cross-section that accommodates the body width and the end widths, the cross-section including a first portion and a second portion; and
   wherein the second portion of the cross-section is open to the perimeter of the inner tubular element along a longitudinal axis of the inner tubular element.

9. The system of claim 8, wherein the outer sheath has a slot, whereby rotating one or both of the outer sheath and the inner tubular element relative to each other to align the slot with the second portion of the cross-section allows at least one anchor of the distal end and the proximal end of the elongate flexible element to deploy radially outward from the outer sheath.

10. The system of claim 8, wherein the outer sheath has a slot, whereby sliding one or both of the outer sheath and the inner tubular element relative to each other to align the slot with the second portion of the cross-section allows at least one anchor of the distal end and the proximal end of the elongate flexible element to deploy radially outward from the outer sheath.

11. The system of claim 8, wherein the cross-section is substantially T-shaped and wherein the first portion of the cross-section is configured to slidingly accept the body portion of the elongate flexible element and the second portion of the cross-section is configured to slidingly accept the distal end and proximal end of the elongate flexible element.

12. The system of claim 8, wherein the cross-section is substantially C-shaped and wherein the first portion of the cross-section is configured to slidingly accept the body portion of the elongate flexible element and the second portion of the cross-section is configured to slidingly accept the distal end and proximal end of the elongate flexible element.

13. The system of claim 8, wherein the distal end and the proximal end each comprise one or more tissue anchors selected from the group consisting of tines, forks, hooks, fingers, barbs, loops and clips.

14. A tissue retractor system, comprising:
a delivery catheter comprising:
an inner tubular element with a lumen therethrough;
an outer sheath disposed about the inner tubular element, the outer sheath and inner tubular element slidingly disposed relative to each other; and
an elongate flexible element configured to transition between a first configuration when constrained and a second bowed configuration when unconstrained, the elongate flexible element disposed within the lumen of the inner tubular element, the elongate flexible element and inner tubular element slidingly disposed relative to each other and the outer sheath comprising:
a distal end having an end width and configured to engage a first target tissue portion;
a proximal end having an end width and configured to engage a second target tissue portion; and
a body portion having a body width connecting the distal end to the proximal end,
wherein the body width is wider than the end width of the distal end and proximal end;
wherein the lumen has a cross-section that accommodates the body width and the end widths, the cross-section including a first portion and a second portion; and
wherein the outer sheath has a slot with a width extending along a longitudinal axis of the outer sheath, and wherein the width of the slot substantially matches the end widths.

15. The system of claim 14, whereby rotating one or both of the outer sheath and the inner tubular element relative to each other to align the slot with the second portion of the cross-section allows at least one anchor of the distal end and the proximal end of the elongate flexible element to deploy radially outward from the outer sheath.

16. The system of claim 14, whereby sliding one or both of the outer sheath and the inner tubular element relative to each other to align the slot with the second portion of the cross-section allows at least one anchor of the distal end and the proximal end of the elongate flexible element to deploy radially outward from the outer sheath.

17. The system of claim 14, wherein the cross-section is substantially T-shaped and wherein the first portion of the cross-section is configured to slidingly accept the body portion of the elongate flexible element and the second portion of the cross-section is configured to slidingly accept the distal end and proximal end of the elongate flexible element.

18. The system of claim 14, wherein the cross-section is substantially C-shaped and wherein the first portion of the cross-section is configured to slidingly accept the body portion of the elongate flexible element and the second portion of the cross-section is configured to slidingly accept the distal end and proximal end of the elongate flexible element.

19. The system of claim 14, wherein the distal end and the proximal end each comprise one or more tissue anchors selected from the group consisting of tines, forks, hooks, fingers, barbs, loops and clips.

20. The system of claim 14, wherein the first portion remains uniform throughout the lumen, and wherein the second portion has a first height dimension at a proximal end of the inner tubular element that transitions into a second height dimension at a distal end of the inner tubular element, wherein the first height dimension is smaller than the second height dimension.

* * * * *